United States Patent
Nikolic et al.

(10) Patent No.: US 7,674,222 B2
(45) Date of Patent: Mar. 9, 2010

(54) CARDIAC DEVICE AND METHODS OF USE THEREOF

(75) Inventors: Serjan Nikolic, San Francisco, CA (US); Alexander Khairkhahan, Palo Alto, CA (US)

(73) Assignee: CardioKinetix, Inc., Menlo Park, CA (US)

( * ) Notice: Subject to any disclaimer, the term of this patent is extended or adjusted under 35 U.S.C. 154(b) by 206 days.

(21) Appl. No.: 11/640,469

(22) Filed: Dec. 14, 2006

(65) Prior Publication Data

US 2007/0161846 A1    Jul. 12, 2007

Related U.S. Application Data

(63) Continuation-in-part of application No. 10/212,033, filed on Aug. 1, 2002, now Pat. No. 7,303,526, which is a continuation-in-part of application No. 09/635,511, filed on Aug. 9, 2000, now abandoned.

(60) Provisional application No. 60/147,894, filed on Aug. 9, 1999.

(51) Int. Cl.
A61B 1/00    (2006.01)
(52) U.S. Cl. .......................................... 600/16; 600/37
(58) Field of Classification Search ......... 623/1.1–2.42; 600/16–18, 37
See application file for complete search history.

(56) References Cited

U.S. PATENT DOCUMENTS

| | | | |
|---|---|---|---|
| 3,874,388 A | 4/1975 | King et al. |
| 4,007,743 A | 2/1977 | Blake |
| 4,425,908 A | 1/1984 | Simon |
| 4,619,246 A | 10/1986 | Molgaard-Nielsen et al. |
| 4,685,446 A | 8/1987 | Choy |
| 4,710,192 A | 12/1987 | Liotta et al. |
| 4,832,055 A | 5/1989 | Palestrant |
| 4,917,089 A | 4/1990 | Sideris |
| 5,104,399 A | 4/1992 | Lazarus |
| 5,192,301 A | 3/1993 | Kamlya et al. |
| 5,192,314 A | 3/1993 | Daskafakis |
| 5,375,612 A | 12/1994 | Cottenceau et al. |
| 5,385,156 A | 1/1995 | Oliva |
| 5,425,744 A | 6/1995 | Fagan et al. |
| 5,433,727 A | 7/1995 | Sideris |
| 5,451,235 A | 9/1995 | Lock et al. |
| 5,496,277 A | 3/1996 | Termin et al. |
| 5,527,337 A | 6/1996 | Stack et al. |

(Continued)

FOREIGN PATENT DOCUMENTS

WO    WO 00/27292    5/2000

(Continued)

OTHER PUBLICATIONS

Khairkhahan et al; U.S. Appl. No. 11/860,438 entitled "Laminar ventricular partitioning device," filed Sep. 24, 2007.

(Continued)

*Primary Examiner*—Scott M Getzow
(74) *Attorney, Agent, or Firm*—Shay Glenn LLP

(57) ABSTRACT

Devices and methods are described herein which are directed to the treatment of a patient's heart having, or one which is susceptible to heart failure, to improve diastolic function.

73 Claims, 16 Drawing Sheets

U.S. PATENT DOCUMENTS

| | | |
|---|---|---|
| 5,527,338 A | 6/1996 | Purdy |
| 5,549,621 A | 8/1996 | Bessler et al. |
| 5,578,069 A | 11/1996 | Miner, II |
| 5,634,936 A | 6/1997 | Linden et al. |
| 5,634,942 A | 6/1997 | Chevillon et al. |
| 5,702,343 A | 12/1997 | Alferness |
| 5,709,707 A | 1/1998 | Lock et al. |
| 5,791,231 A | 8/1998 | Cohn et al. |
| 5,797,849 A | 8/1998 | Vesely et al. |
| 5,797,960 A | 8/1998 | Stevens et al. |
| 5,829,447 A | 11/1998 | Stevens et al. |
| 5,833,698 A | 11/1998 | Hinchliffe et al. |
| 5,836,968 A | 11/1998 | Simon et al. |
| 5,843,170 A | 12/1998 | Ahn |
| 5,861,003 A | 1/1999 | Latson et al. |
| 5,865,730 A | 2/1999 | Fox et al. |
| 5,865,791 A | 2/1999 | Whayne et al. |
| 5,871,017 A | 2/1999 | Mayer |
| 5,875,782 A | 3/1999 | Ferrari et al. |
| 5,876,325 A | 3/1999 | Mizuno et al. |
| 5,876,449 A | 3/1999 | Starck et al. |
| 5,879,366 A | 3/1999 | Shaw et al. |
| 5,882,340 A | 3/1999 | Yoon |
| 5,910,150 A | 6/1999 | Saadat |
| 5,916,145 A | 6/1999 | Chu et al. |
| 5,924,424 A | 7/1999 | Stevens et al. |
| 5,925,062 A | 7/1999 | Purdy |
| 5,925,076 A | 7/1999 | Inoue |
| 5,928,260 A | 7/1999 | Chin et al. |
| 5,961,440 A | 10/1999 | Schweich, Jr. et al. |
| 5,961,539 A | 10/1999 | Northrup, III et al. |
| 5,984,917 A | 11/1999 | Fleischman et al. |
| 6,024,096 A | 2/2000 | Buckberg |
| 6,024,756 A | 2/2000 | Huebsch et al. |
| 6,045,497 A | 4/2000 | Schweich, Jr. et al. |
| 6,059,715 A | 5/2000 | Schweich, Jr. et al. |
| 6,076,013 A | 6/2000 | Brennan et al. |
| 6,077,214 A | 6/2000 | Mortier et al. |
| 6,077,218 A | 6/2000 | Alferness |
| 6,093,199 A | 7/2000 | Brown et al. |
| 6,095,968 A | 8/2000 | Snyders |
| 6,096,347 A | 8/2000 | Geddes et al. |
| 6,099,832 A | 8/2000 | Mickle et al. |
| 6,102,887 A | 8/2000 | Altman |
| 6,125,852 A | 10/2000 | Stevens et al. |
| 6,132,438 A | 10/2000 | Fleischman et al. |
| 6,152,144 A | 11/2000 | Lesh et al. |
| 6,161,543 A | 12/2000 | Cox et al. |
| 6,193,731 B1 | 2/2001 | Oppelt et al. |
| 6,221,092 B1 | 4/2001 | Koike et al. |
| 6,231,561 B1 | 5/2001 | Frazier et al. |
| 6,258,021 B1 | 7/2001 | Wilk |
| 6,267,772 B1 | 7/2001 | Mulhauser et al. |
| 6,290,674 B1 | 9/2001 | Roue et al. |
| 6,312,446 B1 | 11/2001 | Huebsch et al. |
| 6,328,727 B1 | 12/2001 | Frazier et al. |
| 6,334,864 B1 | 1/2002 | Amplatz et al. |
| 6,343,605 B1 | 2/2002 | Lafontaine |
| 6,348,068 B1 | 2/2002 | Campbell et al. |
| 6,355,052 B1 | 3/2002 | Neuss et al. |
| 6,360,749 B1 | 3/2002 | Jayaraman |
| 6,364,896 B1 | 4/2002 | Addis |
| 6,387,042 B1 | 5/2002 | Herrero |
| 6,406,420 B1 | 6/2002 | McCarthy et al. |
| 6,419,669 B1 | 7/2002 | Frazier et al. |
| 6,436,088 B2 | 8/2002 | Frazier et al. |
| 6,450,171 B1 | 9/2002 | Buckberg et al. |
| 6,482,228 B1 | 11/2002 | Norred |
| 6,506,204 B2 | 1/2003 | Mazzocchi |
| 6,511,496 B1 | 1/2003 | Huter et al. |
| 6,537,198 B1 | 3/2003 | Vidlund et al. |
| 6,547,821 B1 | 4/2003 | Taylor et al. |
| 6,551,303 B1 | 4/2003 | Van Tassel et al. |
| 6,592,608 B2 | 7/2003 | Fisher et al. |
| 6,652,555 B1 | 11/2003 | Van Tassel et al. |
| 6,685,627 B2 | 2/2004 | Jayaraman |
| 6,730,108 B2 | 5/2004 | Van Tassel et al. |
| 6,852,076 B2 | 2/2005 | Nikolic et al. |
| 6,959,711 B2 | 11/2005 | Murphy et al. |
| 6,994,093 B2 | 2/2006 | Murphy et al. |
| 7,144,363 B2 * | 12/2006 | Pai et al. .................. 600/16 |
| 7,320,665 B2 | 1/2008 | Vijay |
| 2001/0014800 A1 | 8/2001 | Frazier et al. |
| 2002/0019580 A1 | 2/2002 | Lau et al. |
| 2002/0026092 A1 | 2/2002 | Buckberg et al. |
| 2002/0028981 A1 | 3/2002 | Lau et al. |
| 2002/0032481 A1 | 3/2002 | Gabbay |
| 2002/0055767 A1 | 5/2002 | Forde et al. |
| 2002/0055775 A1 | 5/2002 | Carpentier et al. |
| 2002/0111647 A1 | 8/2002 | Khairkhahan et al. |
| 2002/0133227 A1 | 9/2002 | Murphy et al. |
| 2002/0161394 A1 | 10/2002 | Macovlak et al. |
| 2002/0169359 A1 | 11/2002 | McCarthy et al. |
| 2002/0169360 A1 | 11/2002 | Taylor et al. |
| 2002/0188170 A1 | 12/2002 | Santamore et al. |
| 2003/0045896 A1 | 3/2003 | Murphy et al. |
| 2003/0050682 A1 | 3/2003 | Sharkey et al. |
| 2003/0050685 A1 | 3/2003 | Nikolic et al. |
| 2003/0105384 A1 | 6/2003 | Sharkey et al. |
| 2003/0109770 A1 | 6/2003 | Sharkey et al. |
| 2003/0120337 A1 | 6/2003 | Van Tassel et al. |
| 2003/0149333 A1 | 8/2003 | Alferness |
| 2003/0181942 A1 | 9/2003 | Sutton et al. |
| 2003/0220667 A1 | 11/2003 | van der Burg et al. |
| 2004/0002626 A1 | 1/2004 | Feld et al. |
| 2004/0034366 A1 | 2/2004 | van der Burg et al. |
| 2004/0044361 A1 | 3/2004 | Frazier et al. |
| 2004/0064014 A1 | 4/2004 | Melvin et al. |
| 2004/0127935 A1 | 7/2004 | VanTassel et al. |
| 2004/0172042 A1 | 9/2004 | Suon et al. |
| 2004/0260331 A1 | 12/2004 | D'Aquanni et al. |
| 2004/0267378 A1 | 12/2004 | Gazi et al. |
| 2005/0007031 A1 | 1/2005 | Hyder |
| 2005/0015109 A1 | 1/2005 | Lichtenstein |
| 2005/0085826 A1 | 4/2005 | Nair et al. |
| 2005/0096498 A1 | 5/2005 | Houser et al. |
| 2005/0113861 A1 | 5/2005 | Corcoran et al. |
| 2005/0154252 A1 | 7/2005 | Sharkey et al. |
| 2005/0177180 A1 | 8/2005 | Kaganov et al. |
| 2005/0197716 A1 | 9/2005 | Sharkey et al. |
| 2005/0216052 A1 | 9/2005 | Mazzocchi et al. |
| 2005/0228434 A1 | 10/2005 | Amplatz et al. |
| 2006/0014998 A1 | 1/2006 | Sharkey et al. |
| 2006/0025800 A1 | 2/2006 | Suresh |
| 2006/0030881 A1 | 2/2006 | Sharkey et al. |
| 2006/0229491 A1 | 10/2006 | Sharkey et al. |
| 2006/0264980 A1 | 11/2006 | Khairkhahan et al. |
| 2006/0276684 A1 | 12/2006 | Speziali |
| 2006/0281965 A1 | 12/2006 | Khairkhahan et al. |
| 2007/0129753 A1 | 6/2007 | Quinn et al. |
| 2007/0162048 A1 | 7/2007 | Quinn et al. |
| 2008/0045778 A1 | 2/2008 | Lichtenstein et al. |

FOREIGN PATENT DOCUMENTS

| | | |
|---|---|---|
| WO | WO 01/30266 | 5/2001 |
| WO | WO 01/78625 | 10/2001 |
| WO | WO 02/30335 | 4/2002 |
| WO | WO 02/071977 A2 | 9/2002 |
| WO | WO 03/007778 | 1/2003 |
| WO | WO 03/073961 A1 | 9/2003 |
| WO | WO 2004/012629 | 2/2004 |
| WO | WO 2004/047679 A1 | 6/2004 |
| WO | WO 2004/100803 A1 | 11/2004 |

| WO | WO 2005/007031 | 1/2005 |

OTHER PUBLICATIONS

Khairkhahan et al; U.S. Appl. No. 11/801,075, entitled "System for improving cardiac function," filed May 7, 2007 (SLG #10078-701.302).

Khairkhahan et al; U.S. Appl. No. 11/800,998, entitled "System for improving cardiac function," filed May 7, 2007 (SLG #10078-701.400).

Di Mattia, et al. Surgical treatment of left ventricular post-infarction aneurysm with endoventriculoplasty: late clinical and functioal results. European Journal of Cardio-thoracic Surgery. 1999; 15:413-418.

Dor, et al. Ventricular remodeling in coronary artery disease. Current Opinion in Cardiology. 1997; 12:533-537.

Dor, V. The treatment of refractory ischemic ventricular tachycardia by endoventricular patch plasty reconstruction of the left ventricle. Seminars in Thoracic and Cardiovascular Surgery. 1997; 9 (2): 146-155.

Dor. Surgery for left ventricular aneurysm. Current Opinion in Cardiology. 1990; 5: 773-780.

Katsumata, et al. An objective appraisal of partial left ventriculectomy for heart failure. Journal of Congestive Hear Failure and Circulator Support. 1999; 1(2): 97-106.

Kawata, et al. Systolic and Diastolic Function after Patch Reconstruction of Left Ventricular Aneurysms. Ann. Thorac. Surg. 1995; 59:403-407.

Khairkhahan et al; U.S. Appl. No. 12/198,010 entitled "Retrievable devices for improving cardiac function," filed Aug. 25, 2008.

Khairkhahan, Alexander; U.S. Appl. No. 12/181,282 entitled "Inflatable ventricular partitioning device," filed Jul. 28, 2008.

Khairkhahan et al; U.S. Appl. No. 12/198,022 entitled "Retrievable cardiac devices," filed Aug. 25, 2008.

Khairkhahan et al; U.S. Appl. No. 12/268,346 entitled "System for improving cardiac function," filed Nov. 10, 2008.

Nikolic, et al., U.S. Appl. No. 12/129,443 entitled "Therapeutic methods and devices following myocardial infarction," filed May 29, 2008.

Khairkhahan et al; U.S. Appl. 12/125,015 entitled "Ventricular partitioning device," filed May 21, 2008.

AGA Medical Corporatioin. www.amplatzer.com/products. "The Muscular VSD Occluder" and "The Septal Occluder" device description. Accessed Apr. 3, 2002.

Gore Medical. www.goremedical.com. "Helex Septal Occluder" product description. Accessed Apr. 3, 2002.

James et al.; Blood Volume and Brain Natriuretic Peptide in Congestive Heart Failure: A Pilot Study; American Heart Journal; vol. 150; issue 5, pp. 984.e1-984.e6 (abstract); Dec. 6, 2005.

Khairkhahan et al; U.S. Appl. No. 12/422,177 entitled "Sealing and filling ventricular partitioning devices to improve cardiac function," filed Apr. 10, 2009.

Khairkhahan et al; U.S. Appl. No. 12/422,144 entitled "System for improving cardiac function by sealing a partitioning membrane within a ventricle," filed Apr. 10, 2009.

* cited by examiner

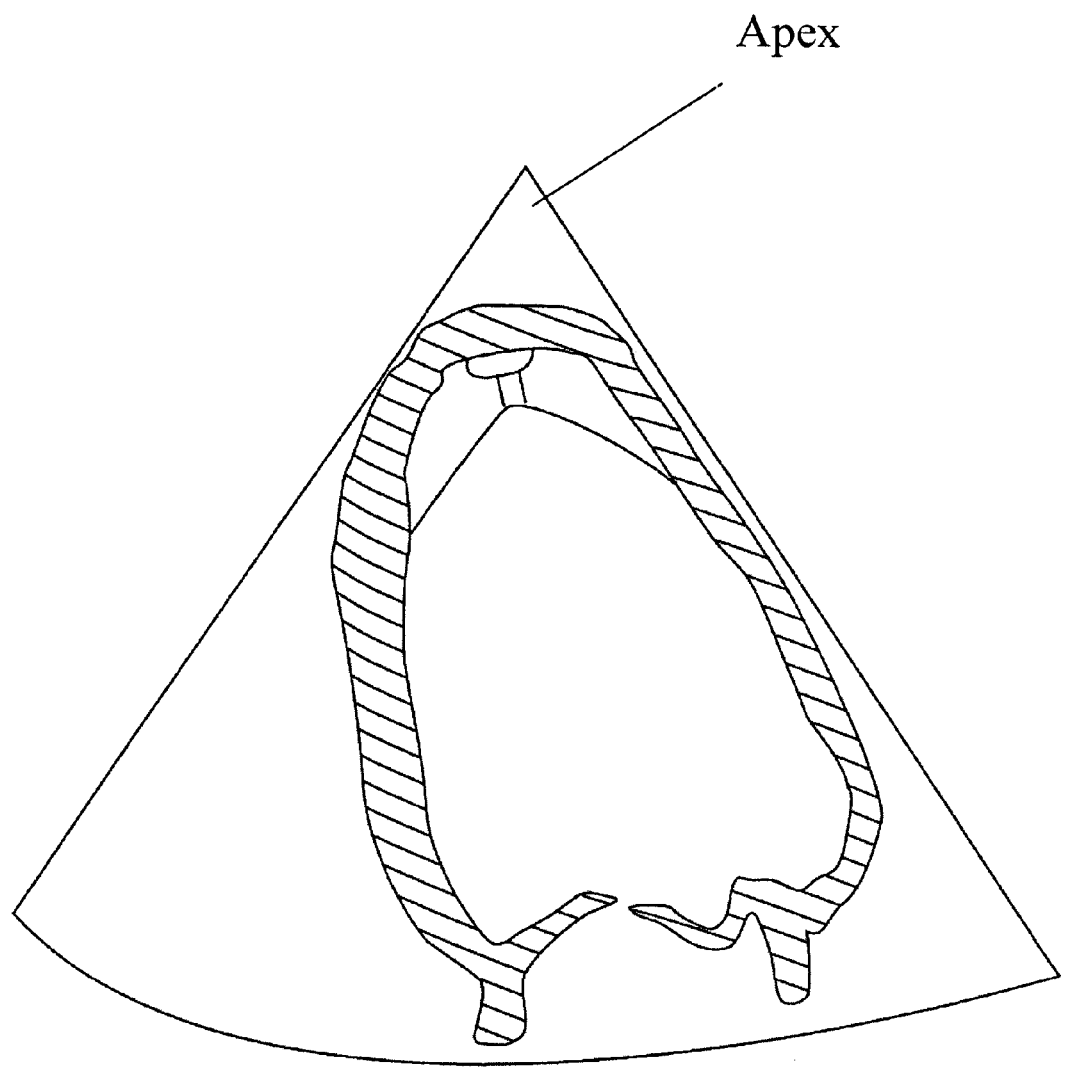
FIG. 18A  Echocardiogram View of Implant at End Diastole

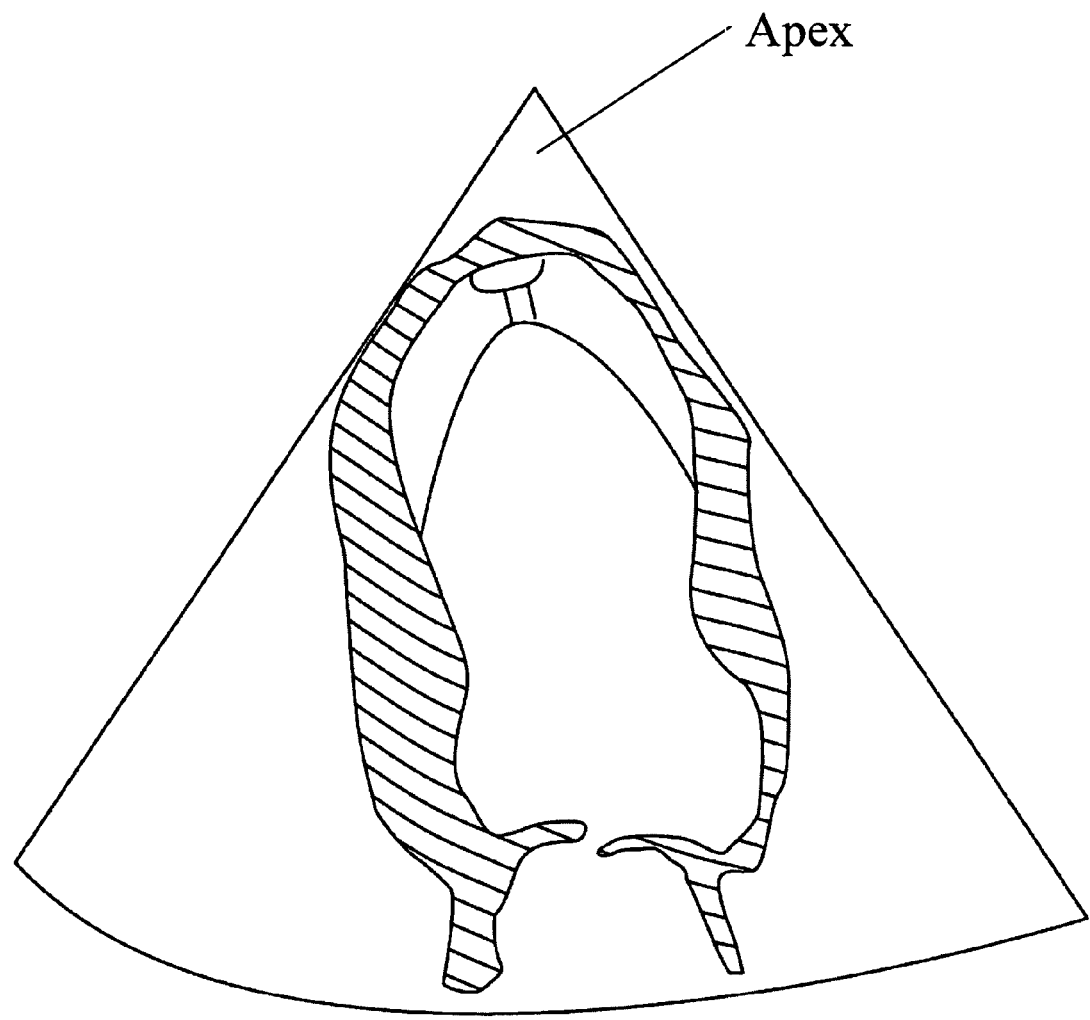
FIG. 18B Echocardiogram View of Implant at End Systole

US 7,674,222 B2

CARDIAC DEVICE AND METHODS OF USE THEREOF

CROSS-REFERENCE

This application is a continuation-in-part application of U.S. patent application Ser. No. 10/212,033, filed Aug. 1, 2002 now U.S. Pat. No. 7,303,526, which is a continuation-in-part of prior U.S. patent application Ser. No. 09/635,511, filed on Aug. 9, 2000, now abandoned, which claims priority from U.S. Provisional Patent Application No. 60/147,894 filed on Aug. 9, 1999; these applications are incorporated herein by reference in their entirety and to which applications we claim priority under 35 USC §120.

BACKGROUND OF THE INVENTION

Heart failure (HF) is one of the most common causes of in-hospital mortality for patients with cardiac diseases. Heart failure is typified by the inability of the heart to pump enough blood to meet the body's metabolic requirements for oxygen and nutrients leading to discrepancies between myocardial oxygen supply and demand.

The left ventricle's inability to generate sufficient cardiac output, i.e. HF, is commonly associated with left ventricular systolic (emptying of left ventricular chamber) dysfunction, but its symptoms may also arise as a result of diastolic (filling of left ventricular chamber) dysfunction (with or without the presence of systolic dysfunction). The term "diastolic dysfunction" refers to changes in ventricular diastolic properties that have an adverse effect on ventricular diastolic pressures and ventricular filling.

An integral part of normal diastolic filling is the contribution of the left ventricular (LV) elastic recoil forces to the LV filling. Elastic recoil forces are generated within healthy myocardium during systolic shortening. The magnitudes of elastic recoil forces are inversely proportional to the volume of the LV, i.e., they increase as the LV volume decreases. Their contribution is important in early diastole because they allow rapid and enhanced early filling by assisting the expansion of the left ventricle.

In a case of ventricular enlargement and/or the decrease of myocardial function due to hypertrophy the left ventricular elastic recoil forces may be diminished or nonexistent, therefore ceasing to assist early ventricular filling and leading to an increase of the ventricular filling pressure.

Intervention to alleviate the resultant symptoms of the physical changes described above may offer great benefit to patients with heart disease. Administration of vasodilators, diuretics, sodium channel blockers, and inotropic agents have been used to reduce the number of acute events and slow the advance of disease, but cannot reverse the physical changes to the heart. Surgical intervention can reduce the volume of the ventricle such that cardiac function is improved but carries high risk for the patient. Other less invasive modes of intervention offer improved function while reducing risk for the patient during and after the procedure.

SUMMARY OF THE INVENTION

The present invention is directed to methods for the treatment of a patient's heart having, or one which is susceptible to, heart failure, in particular, a patient's heart exhibiting diastolic dysfunction. The diastolic dysfunction may be a result of one or more conditions, for example, reduced elastic recoil in the ventricular chamber, more specifically the left ventricle. Diastolic dysfunction is established, for example, by measurements of various echocardiographic parameters such as decreased peak filling velocity and prolonged relaxation time, signs of increased filling pressure, and clinical symptoms of dyspnea and peripheral edema.

In one aspect of the invention a diastolic recoil device is provided which includes a membrane, a hub, preferably centrally located on the diastolic recoil device, and a radially expandable reinforcing frame formed of a plurality of ribs. For example, there may be at least 3 and up to 20 ribs, depending on the application. An elastic, resilient frame may be used. The ribs have distal ends which may be pivotally mounted to the hub and biased outwardly or fixed to the hub, and free proximal ends which are configured to curve or flare away from a center line axis upon expansion of the partitioning device. Tissue penetrating proximal anchors of the free proximal ends are configured to penetrate the tissue lining at an angle 30-120 degrees to the centerline axis of the diastolic recoil device. The tissue penetrating proximal anchors of the ribs may be provided with barbs, hooks, and the like which prevent undesired withdrawal of the tips from the heart wall. The diastolic recoil device and its components may be made with various sizes and diameters. The unconstrained diameter (D, in FIG. 1) of the diastolic recoil device may be about 40 mm to about 100 mm, and the height of the device when expanded (H, in FIG. 1) may range from about 10 mm to about 60 mm, and when collapsed, the diastolic recoil device of any size will fit within a catheter of less than 12 mm for delivery. In some embodiments, the unconstrained diameter of the diastolic recoil device is chosen to be oversized in relationship to the diameter of the ventricle that it is installed within. In one embodiment, a single strand extends around essentially the entire periphery of the membrane so that the flexible periphery of the membrane between each pair of ribs is effectively sealed against the heart wall. The hub may have a distally extending stem with a non-traumatic support component. The distally extending stem with non-traumatic support component together may extend a variable distance from the base of the hub. The stem may extend from about 2 mm to 20 mm from the hub to space the central hub a selected distance from the wall of the ventricle where the diastolic recoil device is seated. In some embodiments, the stem distance can be varied while retaining the same diameter membrane, thus permitting variable partitioning of the volume of the chamber. In some embodiments the support component has a plurality of pods or feet, e.g., at least three, or any number desired to distribute the force of the diastolic recoil device about a region of the ventricular wall surface to minimize, and preferably avoid immediate or long term damage to the tissue of the heart wall, by partitioning necrotic tissue such as tissue of a myocardial infarct (MI), or supporting weakened cardiac wall, and the like.

In another aspect of the invention, a diastolic recoil device adapted for percutaneous delivery to a ventricle of a heart of a patient comprising a plurality of radially expandable ribs connected at their distal ends to a central hub, is implanted in the ventricle of the patient wherein the radially expandable ribs are adapted to provide elastic support between opposing ventricular walls.

In an embodiment of the invention, a diastolic recoil device adapted for percutaneous delivery to a ventricle of a heart of a patient comprising a plurality of radially expandable ribs coupled at their distal ends to a central hub is implanted in the ventricle, wherein the ribs are adapted to augment ventricular wall movement during diastole.

In yet another embodiment of the invention, a diastolic recoil device adapted for percutaneous delivery to a ventricle of a heart of a patient comprising a plurality of radially expandable resilient ribs connected at their distal ends to a central hub and one or more anchor elements at each of the proximal ends of the ribs are adapted to secure the device to a selected area of a wall within the ventricle, wherein the ribs are adapted to support the wall and unload the cardiomyocytes to limit remodeling of the heart.

In another embodiment of the invention, a diastolic recoil device adapted for percutaneous delivery to a ventricle of a heart of a patient comprising a plurality of radially expandable ribs connected at their distal ends to a central hub is implanted in a patient, wherein the ribs are adapted to reduce diastolic pressure of a ventricle of the heart once deployed.

In still another embodiment, a diastolic recoil device adapted for percutaneous delivery to a heart of a patient comprising a plurality of radially expandable ribs connected at their distal ends to a central hub; and a plurality of anchor elements attached to a plurality of said ribs at their proximal ends wherein the anchor elements are adapted to secure the apparatus to a wall of a ventricle of said heart; and, wherein once the device is implanted in a ventricle of a patient, the device is adapted to reduce a volume of the ventricle to improve the pressure-volume relationship of the ventricle.

In another embodiment, a diastolic recoil device comprising a resiliently deformable member and a plurality of anchors, is delivered percutaneously to and anchored within the interior of a ventricle of a patient's heart to span a region of said ventricle, wherein the resiliently deformable member deforms from a first shape to a second shape during systole and to return to the first shape during diastole to assist in expansion of the ventricle.

In other embodiments, a diastolic recoil device comprising a resiliently deformable member and a plurality of anchors, is delivered percutaneously to and anchored within the interior of a ventricle of a patient's heart to span a region of the ventricle, where the resiliently deformable member stores energy during systole and releases stored energy back to a wall of the ventricle in synchrony with a heart cycle.

In some embodiments, a diastolic recoil device further comprises a delayed release spring having either a damped expansion mode or a triggered release such that the release of recoil forces back to the walls of the ventricular chamber can be selectively timed during diastole. This may aid individuals who require additional force to be applied back to ventricular walls during differing portions of diastole.

In yet another embodiment of the invention, a patient may be treated who has no systolic dysfunction, but does have diastolic dysfunction. Devices and methods are provided which utilize a diastolic recoil device having a frame and a hub which can provide force back to the walls of the ventricle. However, the device does not have a membrane as partitioning a portion of the ventricle may not be necessary for these patients. The frame may need differing characteristics to perform, as these patients may require more force to be applied to potentially stiffened and thickened heart walls. Therefore the number of ribs may be increased, the thickness of the ribs may be increased, the stiffness of the ribs may be increased, or the type of alloys or composite of which the frame is made may be different from other devices provided for in this invention. In this embodiment, the device may be seated lower than the base of the papillary muscles in the ventricle. The unconstrained diameter of such a device may be at least about 25 mm to about 90 mm.

In another aspect of the invention, methods are provided which include partitioning a chamber (e.g., left and/or right ventricles) of a patient's heart, exhibiting diastolic dysfunction disorder, or one which exhibits the characteristics of diastolic dysfunction, into a functional portion and an excluded, nonfunctional portion by implanting a diastolic recoil device according to the present invention.

Some embodiments of the invention includes the use of a diastolic recoil device having a partitioning membrane, preferably a reinforced partitioning membrane, with a pressure receiving surface, preferably concave, which defines in part the functional portion of the partitioned heart chamber when implanted or anchored within the patient's heart, in particular, within the ventricle.

In other embodiments of the invention a patient suffering from a heart condition is treated by advancing percutaneously a collapsed diastolic recoil device comprising a plurality of radially expandable ribs connected at their distal ends to a central hub and having an anchor element at the proximal end of each of the ribs; expanding the ribs in a ventricle of the heart; and, securing the device to a selected area of a wall of the ventricle with the anchor elements thereby providing elastic support between opposing ventricular walls. The ribs thus absorbing and releasing recoil forces back to the area of attachment reduce forces directed at the area of the heart in the newly created nonfunctional portion of the ventricle. This reduction eases pressure on a weakened area of a cardiac wall of the nonfunctional portion of the chamber.

The storing and release of energy by the frame occurs in synchrony with the action of the heart. This transfer of energy may decrease the ventricular pressure in diastole, increase the atrio-ventricular pressure gradient, increase filling, and thus improve ejection fraction Dyskinetic or aneurystic ventricular walls result in dyssynchronous behavior during the cardiac cycle, leading to inefficient pumping function. Installation of a device of the invention can remove those dyssynchronous contributions to heart rhythms, restoring overall synchrony in the cardiac cycle, and thus improve ejection fraction.

In yet another embodiment of the method a patient suffering from a heart condition is treated by advancing percutaneously a collapsed diastolic recoil device comprising a plurality of radially expandable ribs connected at their distal ends to a central hub and having an anchor element at the proximal end of each of the ribs; expanding the ribs in a ventricle of the heart; and, securing the device to a selected area of a wall of the chamber with the anchor elements thereby augmenting a ventricular wall movement during diastole.

Another embodiment of the method treats a patient suffering from a heart condition by advancing percutaneously a collapsed diastolic recoil device with a plurality of radially expandable resilient ribs connected at their distal ends to a central hub, and an anchor element at the proximal end of each of the ribs; expanding the ribs in a ventricle of the heart; and, securing the device to a selected area of a wall of the ventricle with the anchor elements wherein the ribs support the ventricular wall, unloading the myocardium, decreasing stress and thus benefiting mechanical function. More efficient function and decreased stress leads to decreased rates of dilation, and hence may limit remodeling of the heart.

Still another method of the invention treats a heart of a patient by advancing percutaneously a collapsed diastolic recoil device comprising a plurality of radially expandable ribs connected at their distal ends to a central hub and having an anchor element at the proximal end of each of the ribs into a ventricle of the heart; expanding the ribs in the chamber of the heart; and, securing the device to a selected area of chamber wall with the anchor elements thereby reducing the diastolic pressure of the ventricle.

In another aspect of the invention methods are provided to reduce mitral valve regurgitation by advancing percutaneously a collapsed diastolic recoil device comprising a plurality of radially expandable ribs connected at their distal ends to a central hub and having an anchor element at the proximal end of each of the ribs; expanding the ribs in a ventricle of the heart; and, securing the device to a selected area of a wall of the ventricle with the anchor elements thereby reducing mitral valve regurgitation.

Another embodiment of the invention is a method of treating a patient suffering from a heart condition by advancing percutaneously to the interior of a ventricle of the patient's heart a diastolic recoil device comprising a resiliently deformable member and a plurality of anchors; securing the device to opposing wall sections of the ventricle with the anchors; deforming the deformable member as the opposing wall sections move toward each other during systole; and providing a recoil force from the deformable member to the wall sections during diastole.

Yet another embodiment is a method of treating a patient suffering from a heart condition by advancing percutaneously to the interior of a ventricle of the patient's heart a diastolic recoil device comprising a resiliently deformable member and a plurality of anchors; securing the diastolic recoil device to opposing wall sections of the ventricle with the anchors; storing energy within the deformable member as the opposing wall sections move toward each other during systole; and releasing energy from the deformable member to the wall sections during diastole.

In some embodiments of the invention, use of the diastolic recoil device or the methods of treatment results in improvement in the ejection fraction of the ventricle. The ejection fraction increase may be at least about 5% up to about 90%.

In some embodiments of the invention, use of the diastolic recoil device or the methods of treatment results in decreasing the left ventricle (LV) functional chamber by about 10% to 40%.

In some embodiments of the invention, use of the diastolic recoil device or the methods of treatment results in decreasing minimum LV pressure during diastole at least by about 5%.

In some embodiments of the invention, use of the diastolic recoil device or the methods of treatment results in decreasing end-diastolic pressure by at least about 5%.

The diastolic recoil device may be installed according to the methods of the invention in about one hour. The implantation of the device according to the methods of the invention requires require periods of about 25 minutes under a fluoroscope to install the partitioning device.

Similarly suitable diastolic recoil devices and methods may be used in the left or right ventricle or other heart chambers.

In some embodiments of the invention, after implantation of a diastolic recoil device of the invention, the left ventricle end systolic volume index (LVESVI) of the patient is decreased at least by about 5%.

In other embodiments of the invention, a number of biochemical markers are measured to evaluate cardiac function. One of these, NT-Pro-Brain Natriuretic Peptide (NT-Pro-BNP), is a regulatory peptide which is produced in the ventricle, and is related to the level of stress in myocardium. NT-Pro-BNP is decreased post-implant by at least about 10%.

In some embodiments of the invention, implantation of a partitioning device reverses the decline in ventricular function which may mitigate mitral valve regurgitation and/or decrease the stress on impaired valve leaflets sufficiently to alleviate regurgitation. Diastolic recoil device implantation according to this invention may therefore benefit patients with mitral valve regurgitation from any cause and decreases the regurgitant fraction by at least about 10%.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

FIG. 18A is a drawing of the echocardiograph image of the patient's heart after treatment according to a method of the present invention using a diastolic recoil device at end-diastole, highlighting the effective diameter of the diastolic recoil device in the relaxed state.

FIG. 18B is a drawing of the echocardiograph image of the patient's heart after treatment according to a method of the present invention using a diastolic recoil device at end-systole, highlighting the effective diameter of the diastolic recoil device in the constrained state.

DETAILED DESCRIPTION OF THE INVENTION

Figure 1:
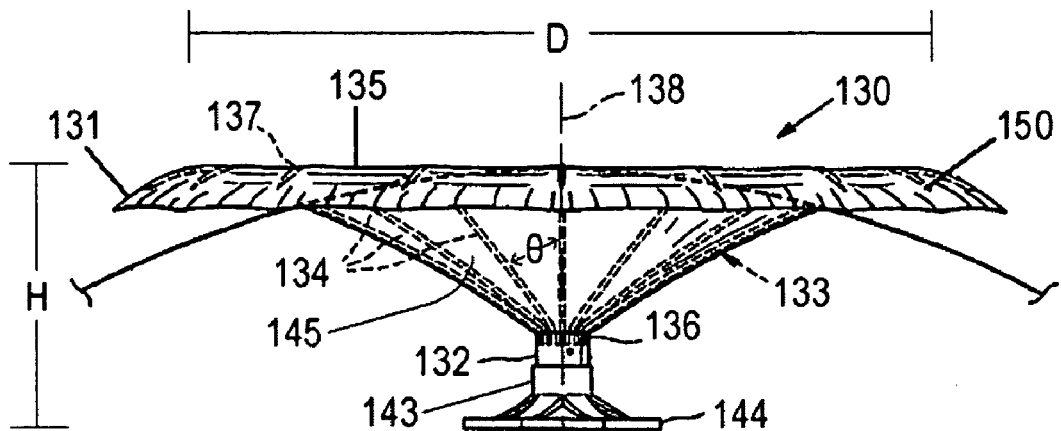
FIG. 1 is an elevational view of a partitioning device embodying features of the invention in an expanded configuration.

The present invention is directed to devices and methods for the treatment of a patient's organ such as a heart. In some cases the heart is susceptible to or experiencing diastolic dysfunction, mitral valve regurgitation or heart failure.

Diastole is the phase of cardiac cycle during which relaxation of the heart muscles occurs after ejecting blood into general circulation and is governed by active and passive properties of the myocardium, geometrical characteristics of the chamber and external forces.

In the cardiac cycle left ventricular diastolic filling begins with opening of the mitral valve as pressure in the ventricle falls below pressure in the atrium. As the ventricle begins to contract the pressure in the ventricle soon exceeds that of the atrium and the mitral valve closes, which marks the end of diastole. The ventricular pressure and volume at this point are referred to as end-diastolic pressure ("EDP") and end-diastolic volume ("EDV"), and the beginning of ventricular systole.

The rate and amount of left ventricular diastolic filling depends upon the positive pressure upstream of the left ventricle provided by venous return and decreasing pressure provided within the left ventricle by expansion of the ventricle during diastole. A reduction in ventricular compliance (i.e., increase in stiffness of ventricular heart wall) may result in less diastolic expansion of the ventricle, less ventricular filling (i.e. decreased end-diastolic volume EDV) and a greater diastolic pressure, resulting in a change in the ventricular diastolic pressure-volume characteristics. In a case of ventricular enlargement and/or the decrease of myocardial function, the left ventricular elastic recoil forces may be diminished, therefore leading to increase of the ventricular filling pressure.

Diastolic dysfunction may also be caused by changes in the rate and degree of left ventricular relaxation, which as stated above, in part is an active process. Several factors can affect left ventricular relaxation, including inotropic stimulation, fast heart rates, non-uniform heart activation and altered timing of all the forces that oppose ventricular ejection. Since calcium uptake by the sarcoplasmic reticulum is energy-dependent, any process that decreases the availability of high-energy phosphates, such as ischemia or hypoxia, also impairs myocardial relaxation.

Diastolic dysfunction is established, for example, by measurements of various echocardiographic parameters such as decreased peak filling velocity and prolonged relaxation time, signs of increased filling pressure and clinical symptoms of dyspnea and peripheral edema.

The devices and methods herein can be used to treat a patient's heart suffering from a diastolic dysfunction disorder or a condition exhibiting the characteristics of diastolic dysfunction. The devices and methods herein involve implanting within the ventricle a device whose shape elastically distorts during systole and recoils during diastole to augment the ventricle's natural recoil action. In one embodiment, the device also partitions the patient's ventricle into a functional portion and an excluded, non-functional portion. The method may be used to treat a heart, in particular the left ventricle, which is exhibiting signs of diastolic dysfunction. Diastolic dysfunction may evidence itself by portions of the chamber becoming dilated, dyskinetic or akinetic, depending on the particular pathology inducing damage to the heart.

A. Device

FIG. 1 illustrates a diastolic recoil device 130 which embodies features of the invention and which may be utilized in practicing the methods herein. The device 130 includes hub 132, preferably centrally located on the diastolic recoil device, and a radially expandable reinforcing frame 133 formed of a plurality of ribs 134 connected at their distal end to the hub. Alternative embodiments of the devices herein include at least three ribs. The ribs form an elastic frame and can be made of material such as, for example, Nitinol stainless steel, titanium alloys, NiTi alloy, other metal alloys, or plastic composites. In some cases, the ribs/frame are made of a material which allows for compression of the free proximal ends towards the central axis during delivery and self expansion upon deployment (e.g. in the patient's heart). The ribs 134 have distal ends 136 which may be pivotally mounted to the hub 132 and biased outwardly or fixed to the hub, and free proximal ends 137 which are configured to curve or flare away from a center line axis 138 at least upon expansion of the diastolic recoil device.

Proximal ends 137 of ribs 134 in their expanded configuration angle outwardly from the hub at an angle θ of about 20-90° away from a centerline axis 138 of the device. The free proximal ends 137 curve outwardly so that the membrane when secured to the ribs of the expanded frame forms a trumpet-shaped concave pressure receiving surface.

Proximal ends 137 of ribs 134 can include anchors 150 configured to engage, and preferably penetrate into, the target tissue (e.g. endocardium of heart chamber to be partitioned, i.e. a ventricle). This enables the securing of a peripheral edge of the diastolic recoil device to the heart wall and fixation of the diastolic recoil device within the chamber so as to partition the chamber into two portions. Anchors 150 are configured to penetrate the tissue lining at an angle ranging from 30-120 degrees to the centerline axis 138 of the partitioning device. Anchors 150 can include barbs, hooks and the like which prevent undesired withdrawal of device 130 from the target tissue.

A membrane 131 can be attached to the ribs 134 of the frame. Membrane 131 can be made of a porous material, for example, expanded polytetrafluoroethylene (ePTFE, or GORE-TEX®, one commercially available product) or a non-porous material. When membrane 131 is porous, it facilitates tissue ingrowth after deployment in the non-functional portion of the heart chamber. Membrane 131 can also be formed from other mesh materials including metals, alloys, or composites. In some cases Membrane 131 is formed from a biocompatible polymeric material such as nylon, polyethylene terephthalate (PET) or polyesters such as hytrel. While not shown in detail, the membrane 131 has a first layer secured to the concave face of the frame formed by the ribs 134, which creates a pressure receiving surface 135. When the diastolic recoil device 130 is deployed upon implantation, the pressure receiving surface 135 is presented to the functional portion of the partitioned chamber. The membrane 131 may have a second layer secured to the convex face of the frame formed by the ribs 134, creating a non-pressure receiving surface 145. When the diastolic recoil device 130 is deployed, the non-pressure receiving surface 145 is presented to the non-functional portion of the partitioned chamber. The manner of application of the layers of membrane to the ribs is described in co-pending application Ser. No. 10/913,608, filed on Aug. 5, 2004, entitled "Ventricular Partitioning Device", assigned to the assignee of the present invention, and incorporated herein by reference in its entirety.

The hub 132 shown in FIG. 1 preferably has a distally extending stem 143 with a non-traumatic support component 144. The distally extending stem 143 with non-traumatic support component 144 together may extend a variable distance from the base of the hub 132, in order to space the device a selected distance from the wall of the chamber where the device is to be seated, thus permitting variable partitioning of the volume of the chamber. The stem 143 and support component 144 together may extend from about 3 mm to about 15 mm from the central hub 132 to isolate differing proportions of the chamber or to provide suitable fits for differing size hearts.

Diastolic recoil devices according to the present invention have several distinct configurations. The unconstrained configuration is measured prior to any constriction or installation within a patient, and represents the largest diameter possible. For example, the diameter (D) as shown in FIG. 1 of a device in its unconstrained configuration is at least 35 mm, up to about 100 mm, and its height (H) is at least 10 mm, to about 60 mm, as needed to fit within the heart of a patient as more fully discussed below. When in its collapsed configuration, a diastolic recoil device has a diameter of less than 12 mm, such that it fits in a catheter for endovascular delivery. Once a diastolic recoil device has been implanted into a chamber of the heart, the flexible and resilient nature of the frame yields two further configurations. The largest installed configuration occurs at the end of diastole, and is referred to as End Diastole Diameter (EDD). The smallest installed configuration occurs at the end of systole, when the chamber is compressed to its smallest size, and this diameter is referred to as the End Systole Diameter (ESD).

Prior to the implantation procedure (as described further below), the diastolic recoil device implant is matched to the size of the left ventricle (e.g., the chamber into which it will be implanted) by comparing the left ventricle end-diastolic diameter at the level of the base of the papillary muscles ("landing zone" diameter) to the unconstrained diastolic recoil device diameter. In order to maximize the occurrence of a permanent seal between the implant and the endocardium, the unconstrained diameter of the selected diastolic recoil device is oversized as compared to the diameter of the landing zone.

Implantation of the oversized diastolic recoil device results in storing compressive forces in the elastic NiTi frame of the device. The origin of compressive forces is a bending deformation of the resilient frame ribs. The decrease of the unconstrained frame diameter to the landing zone diameter is associated with a radial tip displacement of each frame rib while the opposite end of the rib is fixed to the hub of the frame, therefore causing a flexing deformation of the ribs and a rebounding force attempting to return the frame to the unconstrained diameter. These outward recoil forces are transmitted to the myocardium via proximal ends of the ribs implanted into the myocardium, thus applying pressure against the wall of the ventricle. In some embodiments, the unconstrained diameter of the diastolic recoil device is selected to be oversized by at least about 10% up to about 60% over the diameter of the landing zone. The diastolic recoil device is elastic and its configuration changes from a small diameter at end-systole (ESD) to a larger diameter (EDD) at end-diastole. The compression of the diastolic recoil device from end-diastolic to end-systolic configuration causes additional compressive forces to be stored in the elastic frame of the device and is preferably designed to be substantially equivalent at end systole to the elastic restoring forces that originate in the myocardium in a healthy heart. Thus the amounts of outward recoil forces that are transmitted to the walls of the ventricle during diastolic filling are enhanced and augment outward motion of the ventricular walls. The expansion of the ventricle is assisted by the expansion of the ribs to improve diastolic function of the ventricle. Resultantly, stress is decreased in the myocardium, which is beneficial for more efficient mechanical function. As stress is a major cause of dilation, implantation of a device and its contribution of recoil forces back to the heart wall may limit remodeling in the ventricle.

Figure 2:
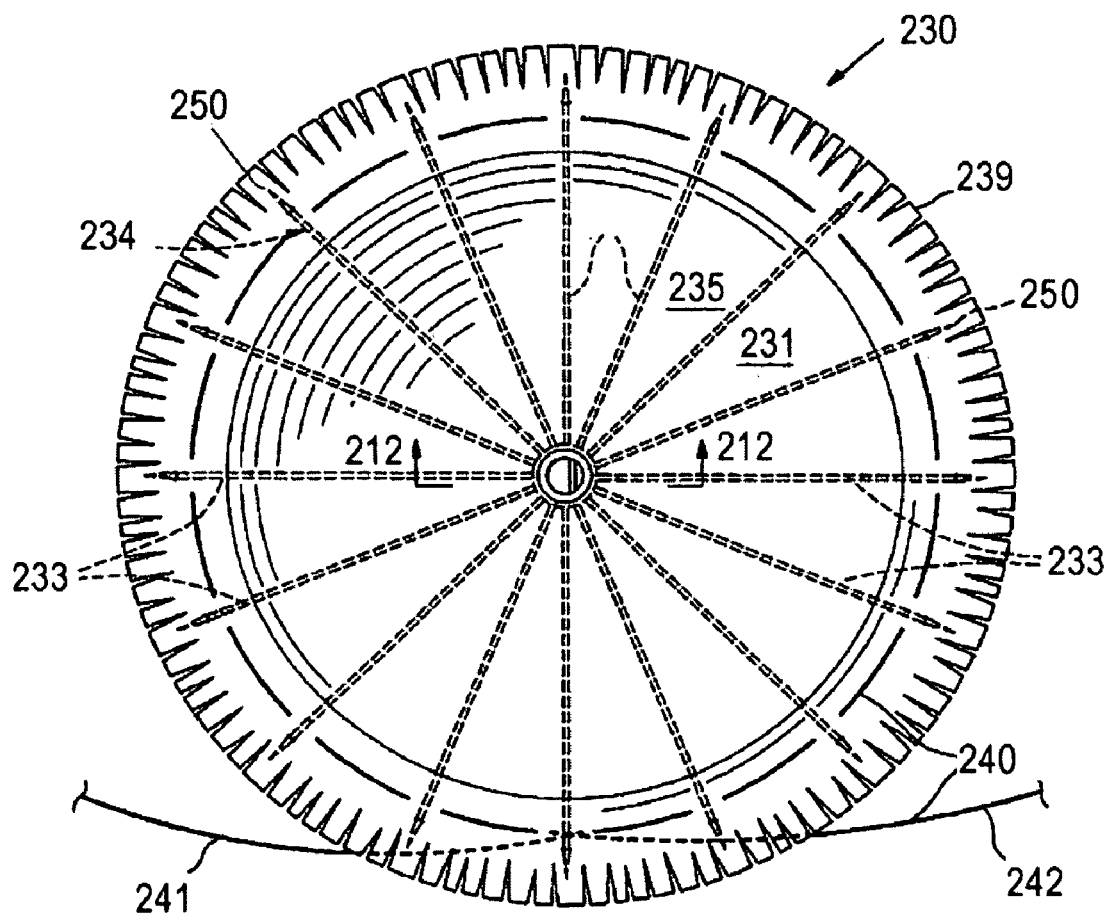
FIG. 2 is a plan view of the diastolic recoil device shown in FIG. 1 illustrating the upper surface of the device.

FIG. 2 illustrates a top view of a diastolic recoil device 230 in its unconstrained configuration, as viewed from above the pressure receiving surface 235. The diastolic recoil device 230 of FIG. 2 has ribs 234 which are radially expandable and connected at their distal end to a central hub. The ribs are adapted to provide an elastic recoil force to a wall of a chamber of a heart (e.g. a left or right ventricle). The ribs store energy during systole and release the stored energy back to the wall of the chamber of the heart in synchrony with the heart cycle. The device 230 further comprises a membrane 231 coupled to the radially expandable ribs 234. At least part of membrane 231 is secured to a pressure receiving side of the frame 233, creating the pressure receiving surface 235. Radial expansion of the free proximal ends 237 unfurls the membrane 231 secured to the frame 233 so that the membrane presents the pressure receiving surface 235 which defines the functional and nonfunctional portions of the chamber. A peripheral edge 239 of the membrane 231 may be serrated as shown in FIG. 2. A serrated edge of peripheral edge 239 in this embodiment helps the membrane spread flat at the periphery. Anchors 250 can include barbs, hooks and the like which prevent undesired withdrawal of device 130 from the wall of the chamber of heart after implantation of the device 230.

The ribs 234 may be individually of variable length and the membrane 231 may be of variable shape suitable to practice the present invention. In some embodiments the membrane 231 and frame 233 define a circular periphery and in other embodiments the membrane 231 and frame 233 define an eccentric or elliptical periphery.

In one embodiment, a strand 240 extends around essentially the entire periphery of the membrane so that the flexible periphery of the membrane between each pair of ribs 234 is effectively sealed against the heart wall. The effectiveness of the seal contributes to facile endothelialization of the pressure receiving surface of a porous membrane. Once endothelialized, the membrane supports regrowth of a new inner wall of the chamber. The expansive strand 240 is formed from material which is stiffer than the flexible, unsupported material of the membrane to provide an outward expansive force or thrust to prevent formation of undesirable inwardly directed folds or wrinkles when the ribs of the diastolic recoil device are in a contracted configuration. A suitable strand 240 is formed from materials such as polypropylene suture or super-elastic NiTi alloy wires. Such strands are typically about 0.005 to about 0.03 inch (about 0.13 to about 0.76 mm) in diameter to provide the requisite outward expansive force when placed in a circular position such as around the periphery of the membrane in less than completely expanded configuration. Ends 241 and 242 of the expansive strand 240 are shown extending away from the diastolic recoil device in FIG. 2. The ends 241 and 242 may be left unattached or may be secured together, e.g. by a suitable adhesive, or to the membrane 231 itself. When the diastolic recoil device is in the collapsed configuration for delivery, the outwardly biased strand 240 ensures that there are no inwardly directed folds or wrinkles and that none are formed when the device is expanded for deployment within the heart chamber. The strand 240 may be several strands of materials as above, rather than just one.

Figure 3:
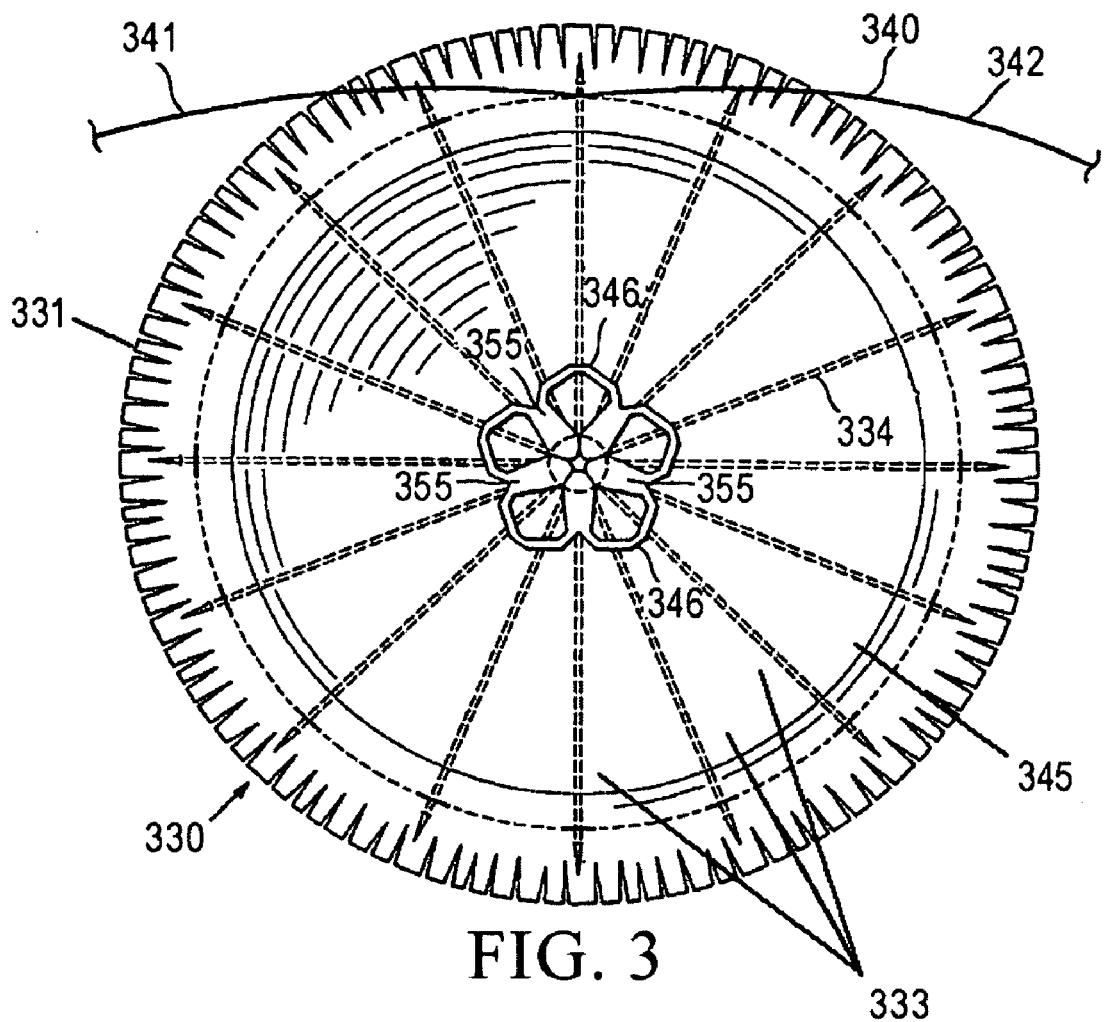
FIG. 3 is a bottom view of a diastolic recoil device.

FIG. 3 is a bottom view of a device 330 herein. The non-pressure receiving surface 345 of the membrane 331 which is secured to the ribs 334 (dotted lines) are illustrated in this view. Extending from the base of the frame 333 are feet 355 which support the device within the non-functional portion of the chamber being partitioned against a wall therein. Feet 355 extend radially and preferably are interconnected by lateral supports 346 which help distribute the force over an expanded area of the surface of the chamber. Feet 355 and lateral supports 346 are made of resilient material which can support the device without causing trauma to the wall of the chamber at contact points. This minimizes or avoids immediate or long term damage to the tissue of the heart wall. The diastolic recoil device can be used to support weakened tissue of damaged heart wall such as necrotic tissue caused by myocardial infarction (MI) and the like.

Figure 4:
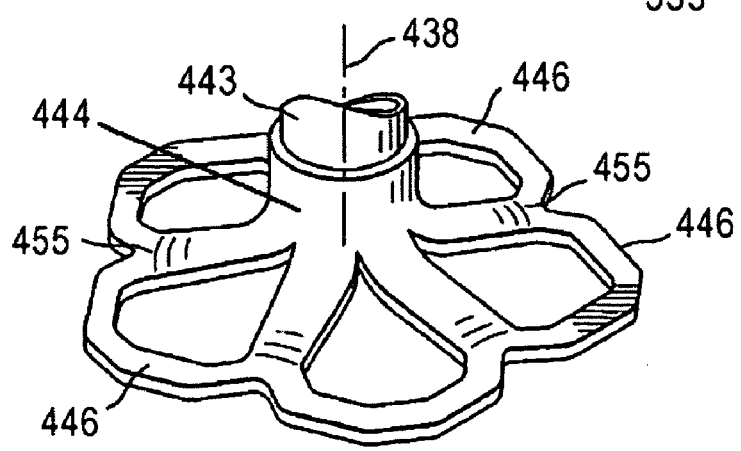
FIG. 4 is a perspective view of one embodiment of a non-traumatic tip of the distally extending stem of a diastolic recoil device.

FIG. 4 is a side view of the support component of the device. The support component 444 has a plurality of feet 455, e.g., at least three or any variable number. The support component 444 atraumatically contacts the wall of the ventricle within the nonfunctional portion of the partitioned ventricle, and distributes direct pressure on the wall to minimize stress on the cardiac wall in the nonfunctional portion of the partitioned ventricle through the feet 455. Support component 444 comprises a stem coupled to a non-traumatic base structure such as the plurality of feet 455 and connected on its other extremity to the stem 443 which extends distally from the non-pressure receiving side of the frame of the device. The support component 444 can vary in length from about 3 mm to about 12 mm such that the non functional portion is sufficiently large in size/volume to partition necrotic tissue, such as tissue of a myocardial infarct (MI), a weakened cardiac wall, or the like. A web of material (not shown) may extend between adjacent feet 445 to provide further support in addition to or in lieu of the supports 446.

Figure 5:
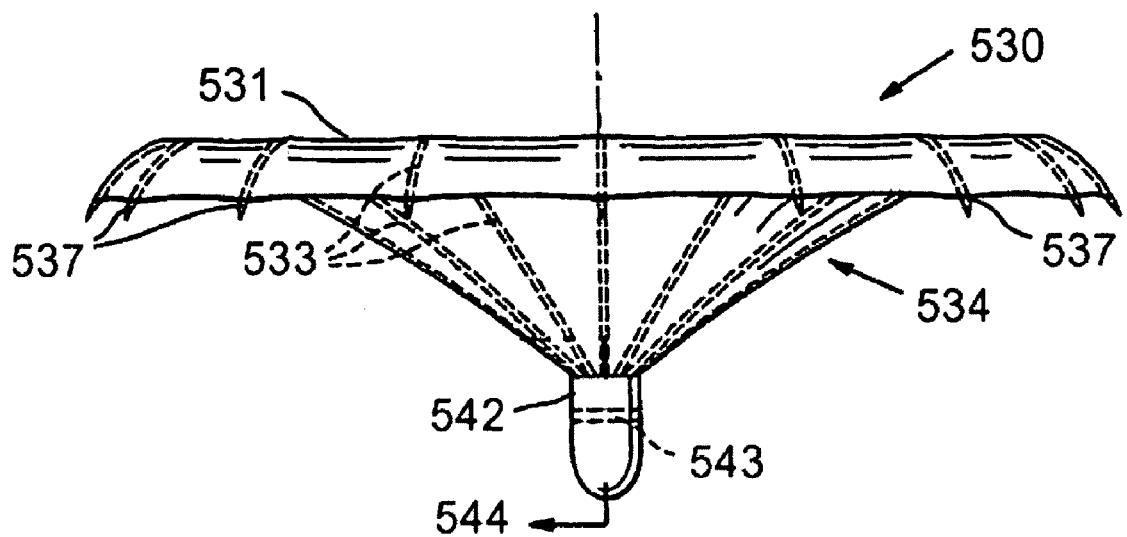
FIG. 5 is an elevational view of a diastolic recoil device embodying an alternative support component of the invention in an expanded configuration.
Figure 6:
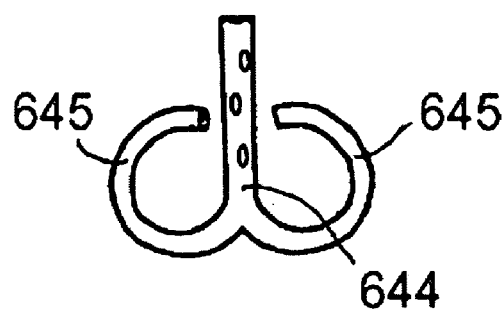
FIG. 6 is a partial elevational view of a diastolic recoil device embodying an alternative support component with curved bumper shaped feet.
Figure 7:
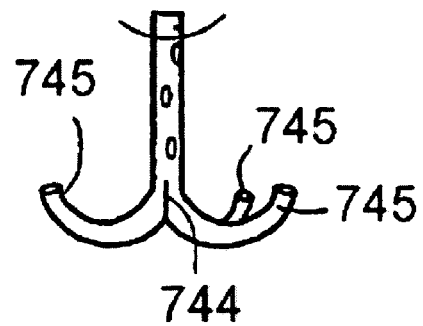
FIG. 7 is a partial elevational view of a diastolic recoil device embodying an alternative support component with J-shaped feet.
Figure 8:
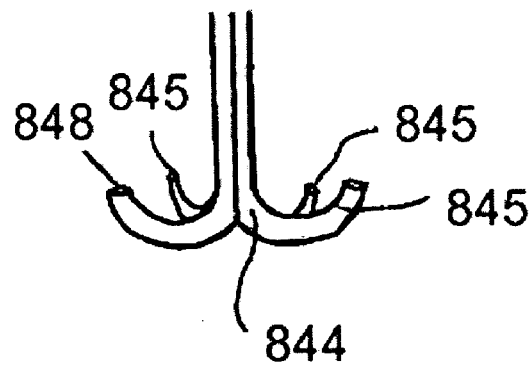
FIG. 8 is a partial elevational view of a diastolic recoil device embodying an alternative support component with J-shaped feet.
Figure 9:
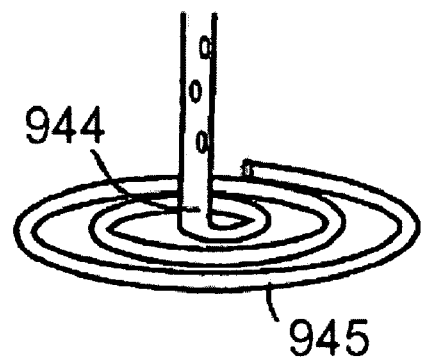
FIG. 9 is a partial elevational view of a diastolic recoil device embodying an alternative support component with J-shaped feet.

Alternative embodiments of the devices comprise feet as shown in FIGS. 5-9. FIG. 5 illustrates a diastolic recoil device 530 comprising a frame 533 with ribs 534. The membrane 531 is attached to the frame 533 and the anchors 537 contact the wall of the chamber to secure the device within the chamber in order to partition it. Device 530 has a nontraumatic support component 544 which has a simple rounded end which is connected to the stem 543. The stem 543 is connected to the central hub 532 which is connected to the frame 533. FIG. 6 illustrates an alternative support component 644 for the devices of the invention. Support component 644 has a plurality of curved bumpers 645 which act as "feet" and contact the wall of the chamber atraumatically. There may be a variable number of curved bumpers to distribute the force that the support component will deliver to the wall of the chamber. FIG. 7 illustrates an alternative support component 744 which has feet such as the plurality of J-bumpers 745. FIG. 8 illustrates a different embodiment of the support component 844 which has a plurality of J-shaped bumpers 845. FIG. 9 illustrates another embodiment of the support component 944 which has a soft, non-traumatic coil 945 which contacts the wall of the heart chamber, and distributes the force from a diastolic recoil device to a larger area of the wall of the heart, reducing strain on weakened or necrotic areas of the chamber.

Figure 10:
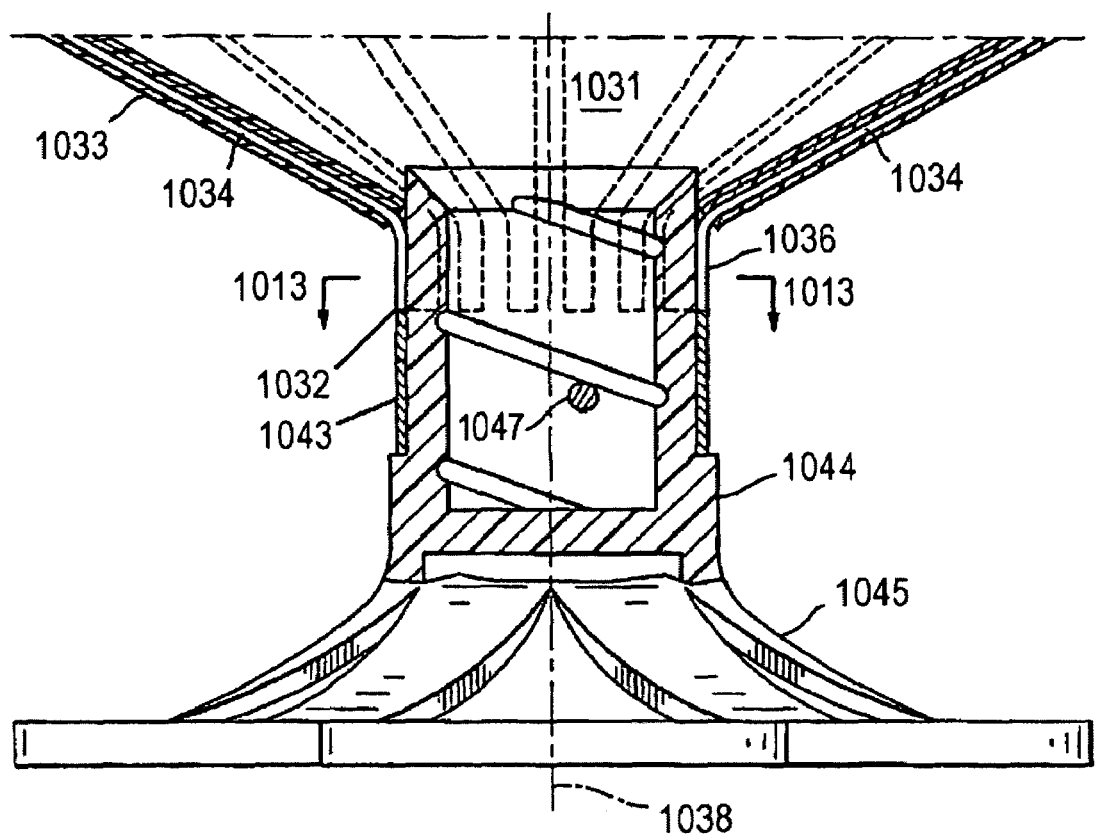
FIG. 10 is a partial cross-sectional view of a lower section of a diastolic recoil device as shown in FIG. 2 taken along the lines 212-212, showing details of connection of the ribs to the hub, the support component, and feet of a diastolic recoil device.
Figure 11:
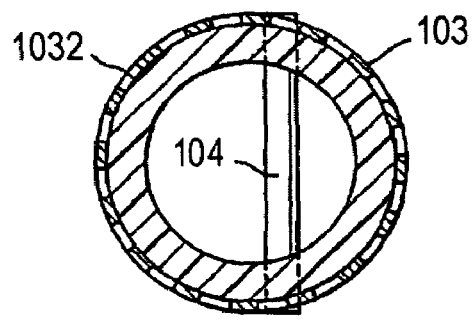
FIG. 11 is a detail cross sectional view of the hub of a diastolic recoil device as shown in FIG. 10, taken along lines 1013-1013.

As shown in FIG. 10 the distal ends 1036 of the ribs 1034 are secured within the hub 1032 and, as shown in the detail of FIG. 11, a transversely disposed connector bar 1047 is secured within the hub which is configured to secure the hub 1032 and thus the diastolic recoil device 1030 to a delivery system such as that described in co-pending applications referenced above. Ser. No. 10/913,608, filed on Aug. 5, 2004, entitled "Ventricular Partitioning Device", assigned to the assignee of the present invention, and incorporated herein by reference in its entirety. This connector bar permits selective connection of the diastolic recoil device to a delivery catheter for delivery within the ventricle, selective placement of the device once within the ventricle to partition the ventricle, selective deployment of the partitioning device and selective release of the diastolic recoil device from the delivery catheter. FIG. 10 also illustrates the connection between connector hub 1032, stem 1043, support component 1044, and feet 1045.

Figure 12:
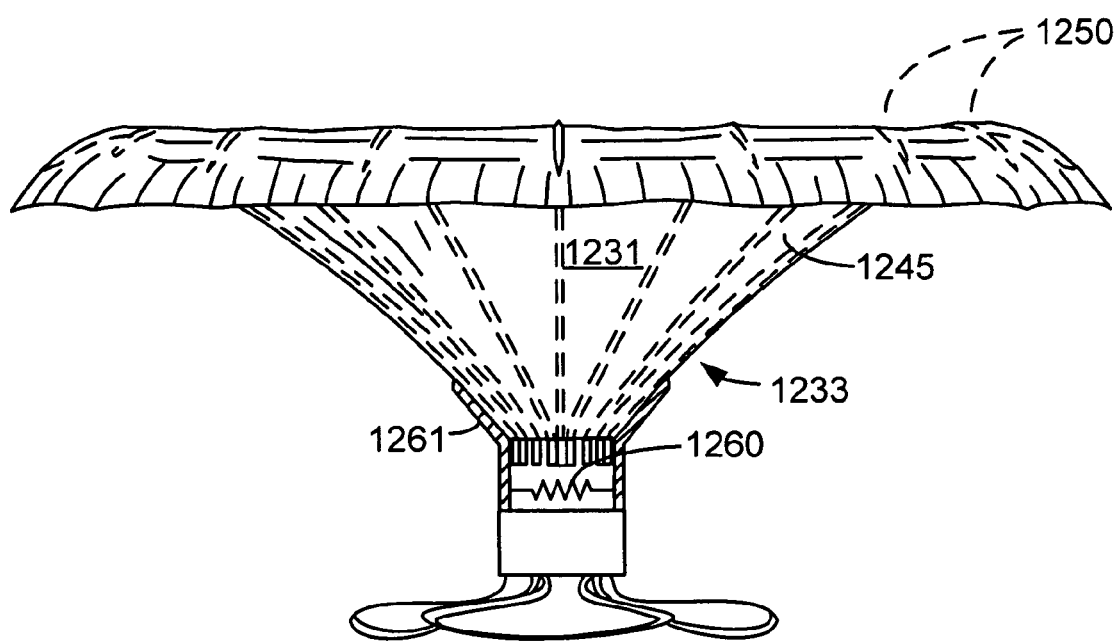
FIG. 12 is a plan view of a diastolic recoil device incorporating a delayed or damped spring release mechanism attached to the pressure bearing side of the frame of the device.

Another embodiment of the invention is envisioned wherein the device is utilized to deliver the recoil energy not throughout the phase of diastolic filling, but at selected time intervals during filling. A device 1230 further incorporating a delayed release spring 1260 as shown schematically in FIG. 12, can be utilized to assist diastolic function. In the top view of device 1230, delayed response spring 1260 is attached to restraint struts 1261 which in turn releasably contact the frame 1233 on the non-pressure bearing side 1245 of the membrane 1231. After installation by anchoring device 1230 to the ventricle walls with anchors 1250, the majority of the recoil force stored in the device is not freely releasable immediately at the end of systole. Instead, the ventricle begins an unassisted expansion while the device is partially secured from freely expanding. At a predetermined point during diastolic expansion, which may be customizable for each patient, the delayed release mechanism is triggered. The restraint struts are 1261 released from contact with the frame 1233, and the stored energy fully released at that point in the cardiac cycle. Thus, the majority of the recoil energy can be given back to the ventricular wall at a select point during diastole, as required for a particular patient. Another embodiment of this aspect of the invention may have a spring means including only a damped releasing mechanism. In these embodiments, the subsequent contraction of the ventricle during systole re-engages the delayed release spring mechanism or restores the damped spring to restore the contact between the restraint struts 1261 and the frame 1233 when the frame is in the compressed state for further cycles of delayed recoil assistance to the ventricle.

Figure 13:
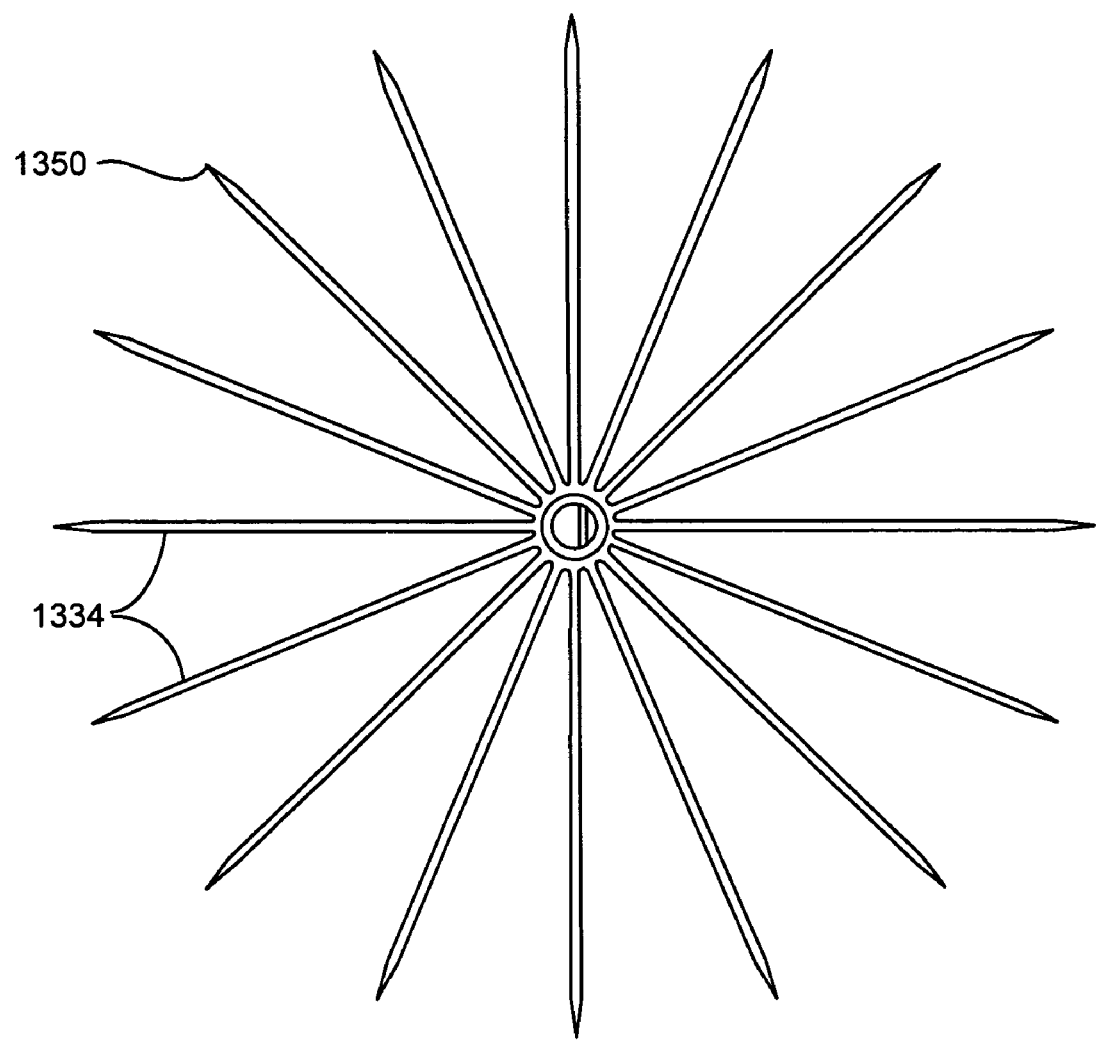
FIG. 13 is a plan view of a diastolic recoil device which includes a frame and a hub but no membrane.
Figure 14:
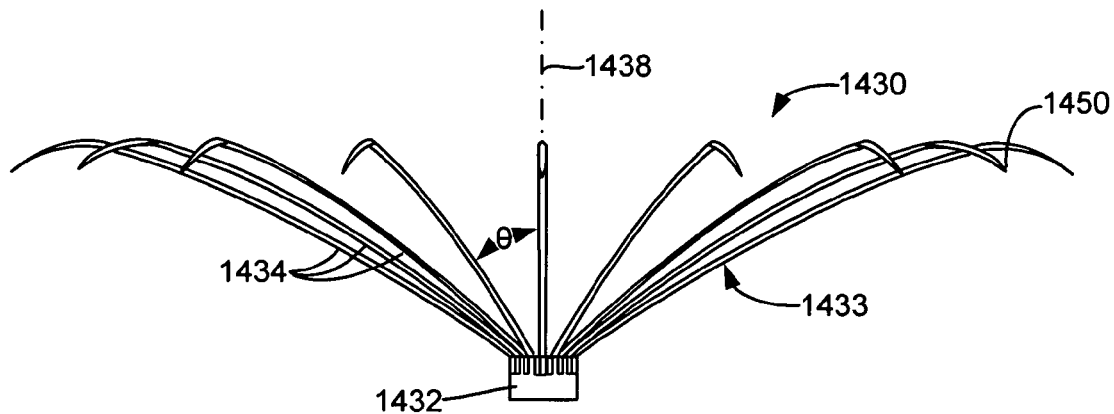
FIG. 14 is an elevational view of the device shown in FIG. 13.
Figure 15A:
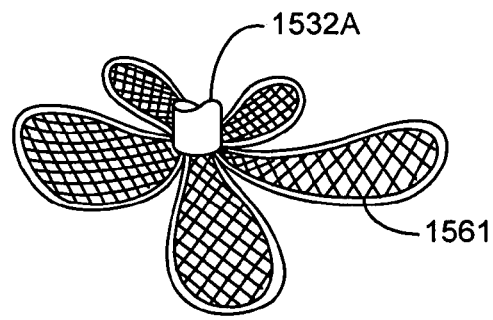
FIG. 15A is a partial elevational view of an alternate basal support for the device shown in FIGS. 13 and 14.
Figure 15B:
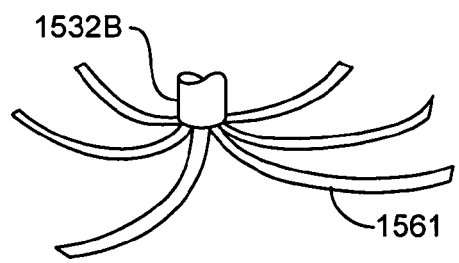
FIG. 15B is a partial elevational view of an alternate basal support for device shown in FIGS. 13 and 14.

Yet another embodiment of the invention can be envisioned for a patient population that has no systolic dysfunction but does have diastolic dysfunction. This population may not have dilation of the heart and partitioning the ventricle to reduce the volume of the ventricle is in this case not necessary. To gain more efficient diastolic filling, a device as shown in FIG. 13 may be utilized, which has a frame 1333 and central hub 1332 as previously described, but which has no membrane. The resilient frame provides force back to the walls of the ventricle and improves the diastolic function of the heart. The frame may need to be different from the frames of other embodiments of this invention, i.e. frame 133 of FIG. 1. In this application, the ventricles of this population of patients may require more force to be applied back to the ventricular walls, which may be thickened and stiffened relative to healthy ventricular walls. It may also be necessary to increase the number of ribs, the thickness of the material of the ribs, the relative stiffness of the ribs, and/or use different alloys or material compositions to form the frame in order to manufacture a device with appropriate resiliency/stiffness properties. The device may seat lower in the ventricular chamber, and may thus require devices with smaller diameters relative to those used for patients with ventricular dilation. The size matching then is made for the end-diastolic diameter of a landing zone at a level further below the base of the papillary muscles. The unconstrained diameter of devices according to this embodiment of the invention may therefore be at least 25 mm up to about 90 mm. The central hub 1432, as shown in the side elevation view of a device depicted in FIG. 14, may not have any distal extension and may ends as a flat disk. A distal extension of hub 1432 may consist of a short rounded nub, or may connect to flexible basal supports which may stabilize the device in its seat in the apex of the ventricle. The basal supports may be configured in many ways. Two examples are given in FIGS. 15A and 15B respectively, shown as basal supports 1561A and 1561B.

Implantation of the devices herein can be accomplished endovascularly or intraoperatively in as little as one hour by a physician or appropriately trained personnel. Such implantation presents limited risk to the patient and requires the patient to be under a fluoroscope for a period of as little as 20 minutes.

Implantation of the diastolic recoil device in the ischemic and enlarged ventricle may bring back the ability of the ventricle to store elastic energy during systole and return this energy in the form of elastic recoil forces during diastole. In an embodiment, this return of energy in the form of elastic recoil may contribute to the improvement of the diastolic function, i.e., decrease of the filling pressure and increase in the magnitude of the early filling in patients with ischemic and/or dilated cardiomyopathy. Thus the ejection fraction of the chamber is increased by at least about a 5% change.

Suitable diastolic recoil device designs useful in the practice of the methods of the present invention have been described in co-pending applications, Ser. No. 11/151,164, filed Jun. 10, 2005, entitled "Peripheral Seal for a Ventricular Partitioning Device"; and Ser. No. 11/199,963, filed Aug. 9, 2005, entitled "Method for Treating Myocardial Rupture;" both of which are assigned to the assignee of the present invention, and incorporated herein by reference in their entirety. Diastolic recoil devices of the present invention are delivered percutaneously or intraoperatively. A suitable delivery device is described in co-pending application Ser. No. 10/913,608, filed on Aug. 5, 2004, entitled "Ventricular Partitioning Device", assigned to the assignee of the present invention, the full disclosure of which is incorporated herein by reference.

The diastolic recoil devices may be conveniently formed by the method described in above-referenced co-pending application Ser. No. 10/913,608 assigned to the assignee of the present invention and which is incorporated herein by reference in its entirety.

B. Uses of the Devices

Figure 16A:
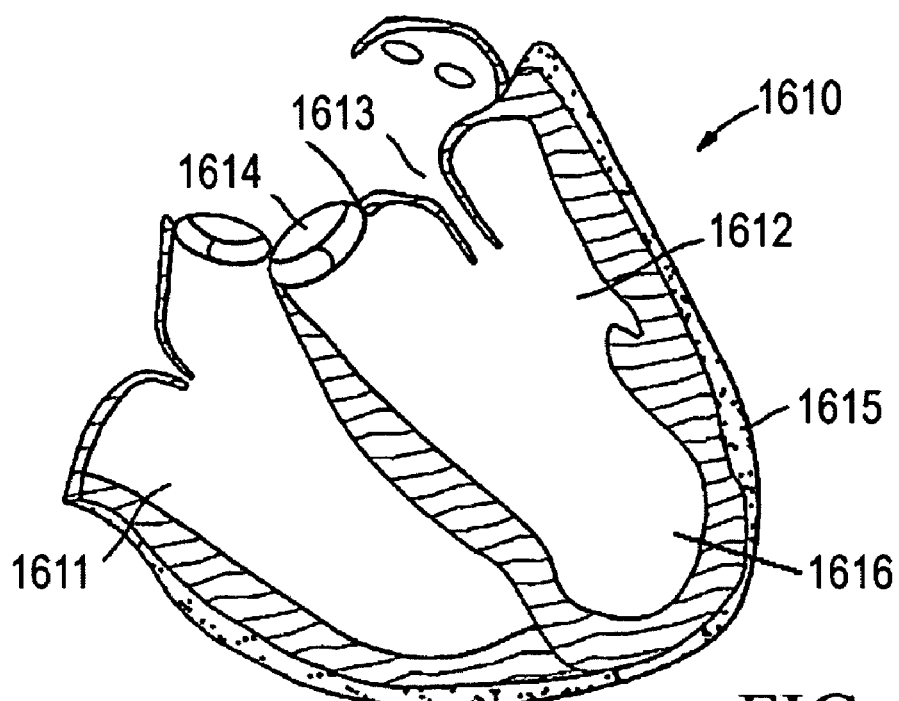
FIG. 16A is a schematic view of a patient's heart exhibiting characteristics of heart failure or incipient CHF.
Figure 16B:
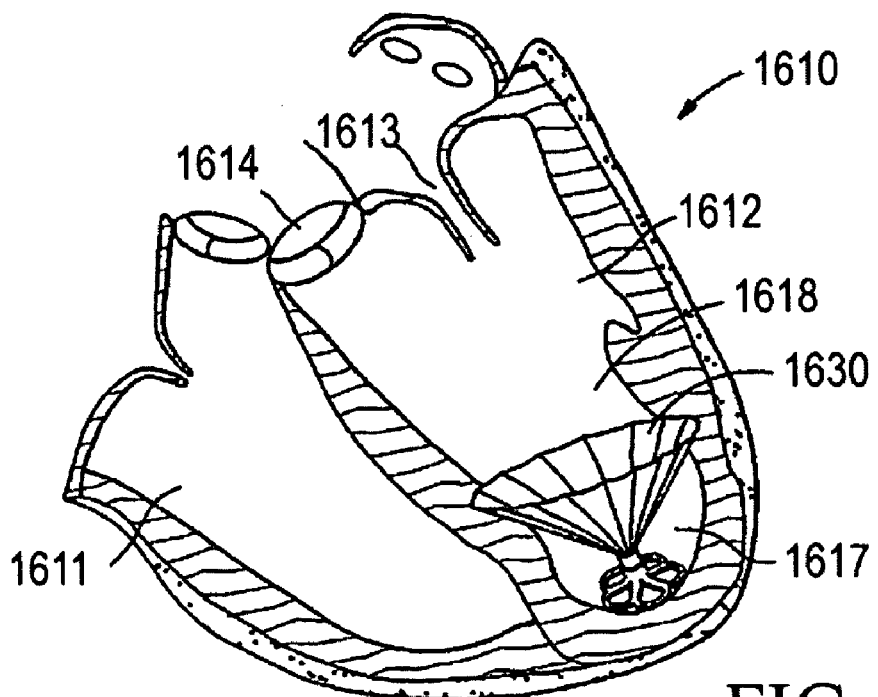
FIG. 16B is a schematic view of the patient's heart of FIG. 16A after treatment according to a method of the present invention using a round shaped diastolic recoil device.
Figure 17:
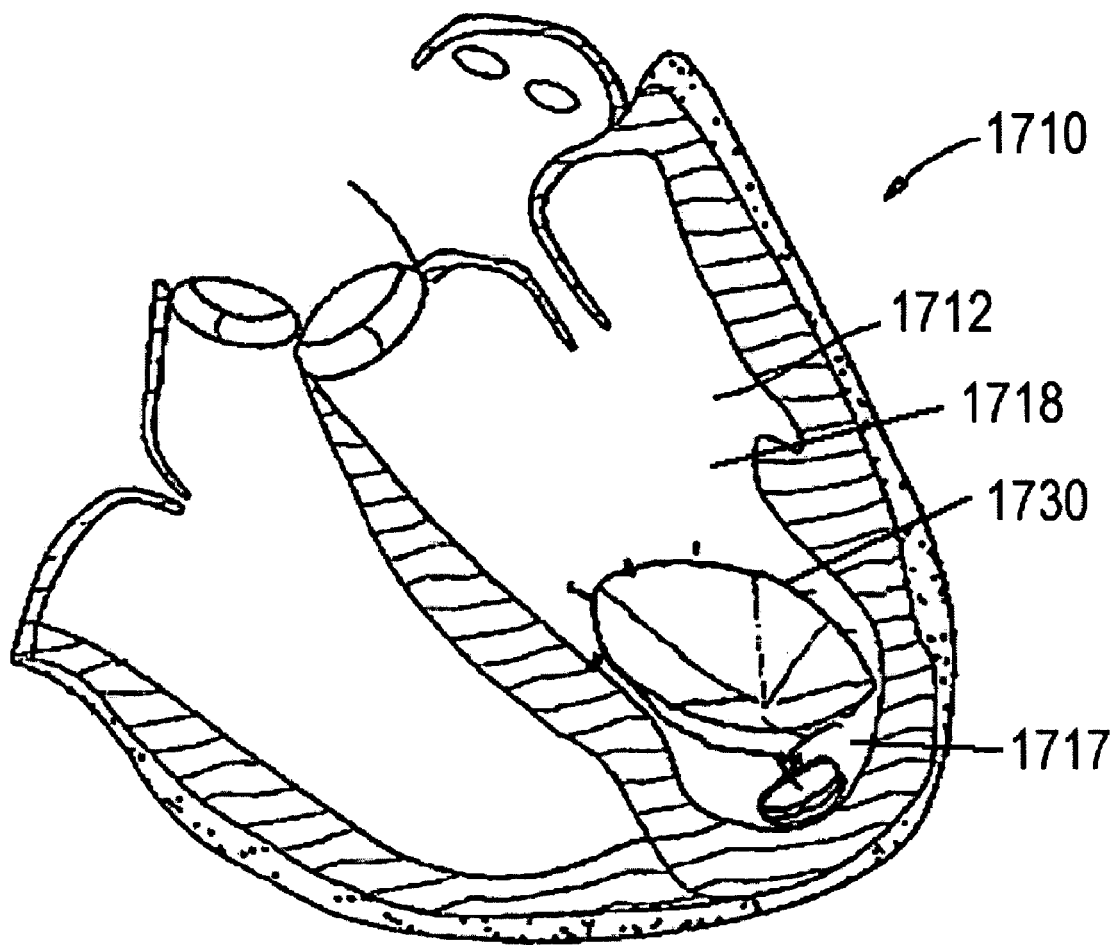
FIG. 17 is a schematic view of the patient's heart of FIG. 16A after treatment according to a method of the present invention using an elliptical shaped diastolic recoil device.

FIG. 16A is a schematic illustration of a patient's heart 1610 showing the right ventricle 1611 and the left ventricle 1612 with the mitral valve 1613 and aortic valve 1614. A pericardium membrane 1615 is shown surrounding the heart 1610. FIG. 16A illustrates a patient's heart with apical dilatation (round enlarged apex 1616 of the LV) which can be found in patients exhibiting characteristics of congestive heart failure. FIG. 16B illustrates the left ventricle 1612 of FIG. 16A after it has been partitioned, with a diastolic recoil device 1630 having features according to the present invention and as described further below, into a main functional or operational portion 1618 and a secondary, essentially non-functional portion 1617. FIG. 17 is a schematic view of the patient's heart of FIG. 16A after treatment according to a method of the present invention using an elliptical shaped diastolic recoil device 1730. The device 1730 is implanted into the left ventricle 1712 of the heart 1710, creating a functional portion 1718 and nonfunctional portion 1717.

FIGS. 18A and 18B are drawings of echocardiograph images of a patient's heart at end-diastole, and end-systole, respectively. The contours of the diastolic recoil device implanted in the left ventricle are visible as fine white lines in the base of the ventricle. Portions of the ribs and periphery can be seen in FIGS. 18A and 18B.

As can be seen from FIGS. 18A and 18B, the diameter of the elastic diastolic recoil device is at its maximal implanted diameter (FIG. 18A) at end-diastole, and at its minimal implanted diameter at end-systole (FIG. 18B). End-systolic diameters (ESD) can be in the range from about 25 mm to about 55 mm. End-diastolic diameters (EDD) can be in the range of about 45 mm to about 70 mm. The compression of the partitioning device from end-diastolic to end-systolic configuration causes elastic recoil forces to be stored in the elastic frame of the device, and to be transmitted to the myocardium during ventricular filling in the outward direction thus enhancing outward motion of the ventricular walls. This storing and release of energy by the frame occurs in synchrony with the action of the heart. This transfer of energy may decrease the ventricular pressure in diastole, increase the atrio-ventricular pressure gradient, increase filling, and thus improve ejection fraction Dyskinetic or aneurystic ventricular walls result in dyssynchronous behavior during the cardiac cycle, leading to inefficient pumping function. Installation of a device of the invention can remove those dyssynchronous contributions to heart rhythms, restoring overall synchrony in the cardiac cycle, and thus improve ejection fraction. In one embodiment of the invention the partitioning device is substantially circular but another embodiment of the invention utilizes an elliptical shaped partitioning device as shown in FIG. 17. Other configurations of the partitioning device are compatible with the construction as described above and with methods to partition a chamber of a heart as set forth here.

The devices herein can be used to treat a patient suffering from a heart condition. Such heart conditions can include, for example, mitral valve regurgitation, myocardial infarction, or scar tissue or akinetic tissue in a heart chamber. A patient can be screened for treatment by the a devices herein by any means known in the art including, but not limited to, measurements of echocardiographic parameters may be such as decreased peak filling velocity and prolonged relaxation time, signs of increased filling pressure, clinical symptoms of dyspnea and peripheral edema, as well as low ejection fraction and a distance a patient can walk in 6 minutes.

Prior to the implantation procedure (as described further below), the diastolic recoil device implant may be matched to the size of the chamber where it is to be inserted (e.g. left ventricle) when the device is to be inserted into the left ventricle this can be accomplished by comparing the left ventricle end-diastolic diameter at the level of the papillary muscles base. This diameter is referred to hereinafter as the landing zone diameter. Measurement of landing zone diameter may be made by any method known in the art including; echocardiography, fluoroscopy, PET, MRI, contrast angiography, and the like, the landing zone diameter is the compared to the relaxed deployed/device diameter. When a device is to be implanted in a ventricle, the ventricle may be dilated such that its end diastolic diameter is greater than 45 mm or even greater than 65 mm. In some cases, to maximize the occurrence of a permanent seal between the implant and the endocardium, the relaxed diameter of the selected diastolic recoil device is oversized as compared to the diameter of the landing zone. The relaxed diameter of the device can be oversized by at least about 10% and up to 60% over the landing zone diameter.

The diastolic recoil device implanted thus decreases the LV volume by at least about 10% up to about 40%. The ratio of the nonfunctional portion to the functional portion, created by partitioning the ventricle by a method of the invention is at least 1:10 or up to about 1:3.

The diastolic recoil device frame is elastic and its diameter changes from a small diameter at end-systole to a larger diameter at end-diastole. The compression of the diastolic recoil device from end-diastolic to end-systolic configuration causes additional compressive forces to be stored in the elastic frame of the device, thus enhancing the ejection fraction of the chamber by at least about 10%, or up to about 90%.

Figure 19:
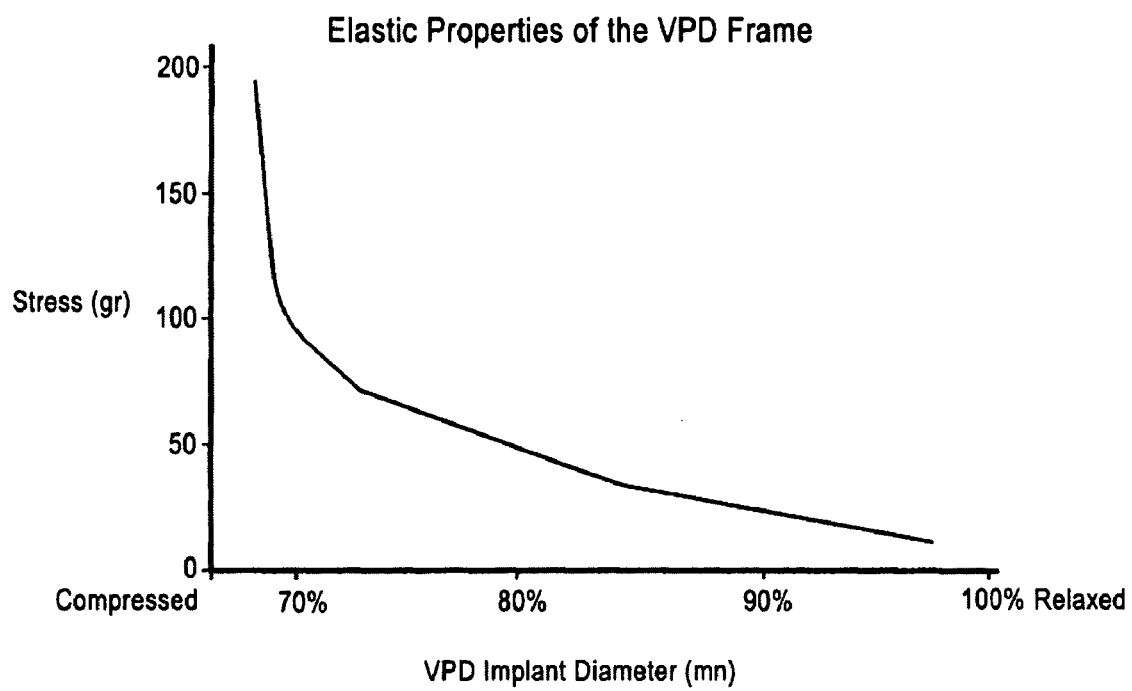
FIG. 19 is a diagrammatical illustration of the elastic characteristics of an embodiment of a diastolic recoil device implant.

The elastic characteristics of the diastolic recoil device implant may be determined by a tensile/compression test, an example of which is diagrammatically shown in FIG. 19. To conduct the test, the diastolic recoil device is positioned inside a custom designed fixture which was connected to a force transducer. The fixture was designed to create substantially equal compressive radial force (compatible with and corresponding to physiological range of forces developed by normal myocardial fibers) on all ribs 34 (as described below) of the implant, thus determining the compression stress-diameter relationship for the frame 33 (as described below) of the device. FIG. 19 shows an exemplary elastic property of the diastolic recoil device. As can be noted from the figure, the magnitude of the elastic recoil forces stored in the diastolic recoil device implant increases as the diastolic recoil device diameter decreases under compression.

It can further be noted that the stiffness of the implant increases in a non-linear fashion as the diameter of the implant decreases as it is compressed to less than 50% of the diameter of the fully relaxed implant.

Figure 20:
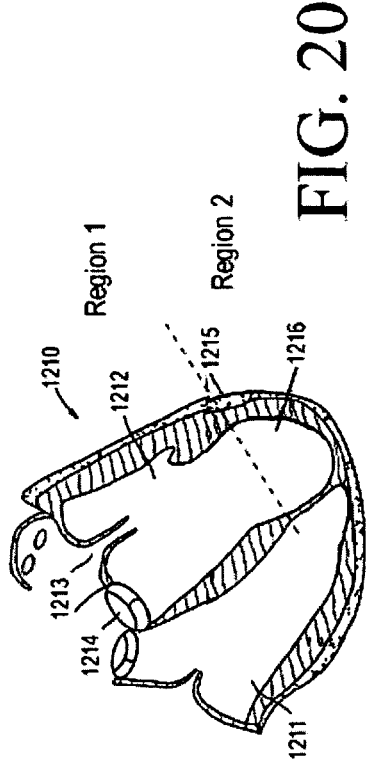
FIG. 20 is a schematic representation of a heart with a ventricle having two distinct regions of myocardium with different contractile properties, Region 1 and Region 2.
Figure 21:
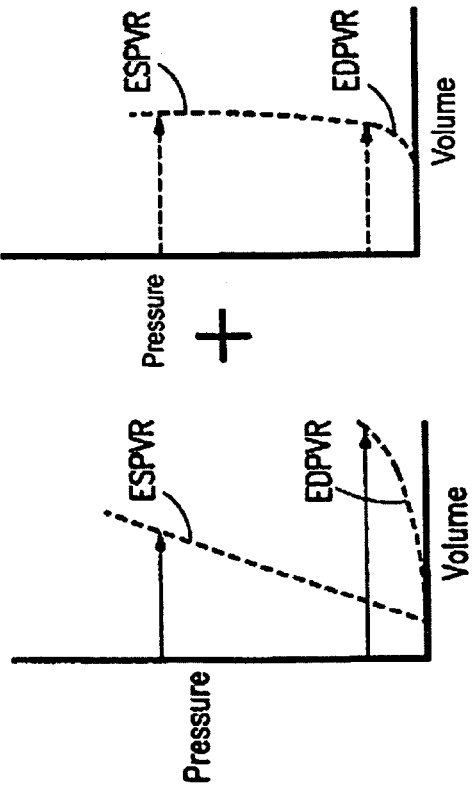
FIGS. 21A-C are diagrammatical representations of the end-systolic pressure volume relationship (ESPVR) and end-diastolic pressure volume relationship (EDPVR) of the ventricle of FIG. 20 prior to installation of a partitioning device.

Modeling experiments can be used to demonstrate the effect of implanting a diastolic recoil device of the invention. FIG. 20 is a schematic representation of a heart with dilation and poor function in the left ventricle, having two distinct regions of myocardium surrounding the interior of the ventricle. Region 1 represents normal myocardium and region 2 represents dilated and dyskinetic or akinetic/myocardium. A simulation experiment is performed, using an elastance model, as described in J H. Artip; et al.; J. Thoracic and Cardiovascular Surg., 122(4), 775-782, 2001. The myocardial properties differ from one region to the next and the global ventricular properties are calculated by the interaction between the two virtual chamber regions, each chamber region having its own pressure volume characteristics. FIGS. 21A-C represent a simulation carried out using a ventricle as in FIG. 20 without a partitioning device. In FIGS. 21A and B, the dashed lines labeled ESPVR (End Systolic Pressure Volume Relationship) represent the maximal pressure that can be developed by that section of the ventricle at any given left ventricular volume. The dashed lines in FIGS. 21A and B labeled EDPVR (End Diastolic Pressure Volume Relationship) represent the passive filling phase for the respective regions of the un-partitioned ventricle, demonstrating the change in volume without great change in pressure, for each simulated region. As can be seen for Region 1 (normal), during systole the pressure changes rapidly relative to volume changes, while during diastole volume changes more rapidly (passive filling) relative to pressure changes. In contrast, in the akinetic region, Region 2, in FIG. 21B, there is no passive filling during diastole, hence the EDPVR is coincident with the ESPVR. Of note is the slope of the ESPVR in Region 2 (FIG. 21B), which is greater than that in Region 1 (FIG. 21A), as the slope is the reciprocal of ventricular compliance. Hence, akinetic Region 2 demonstrates greatly reduced ventricular compliance. The end-systolic pressure-volume relationship (ESPVR) and end-diastolic pressure-volume relationship (EDPVR) for the ventricle of FIG. 20 was determined by the sum (FIG. 21C) of the virtual volumes of the Regions 1 (FIG. 21A) and 2 (FIG. 21B) at each pressure, as shown by the solid lines drawn in FIG. 21C.

Figure 22:
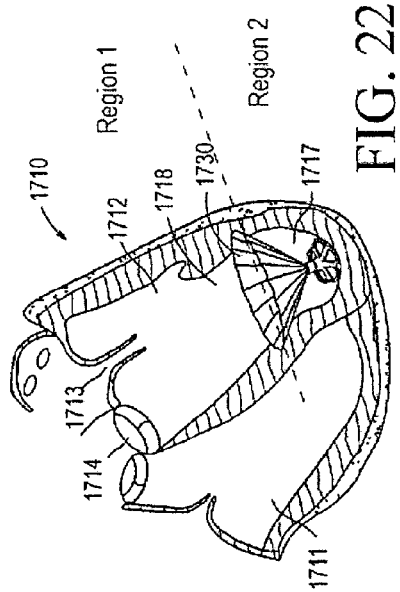
FIG. 22 is a schematic representation of a heart with a ventricle having two distinct regions after installation of a diastolic recoil device.
Figure 23:
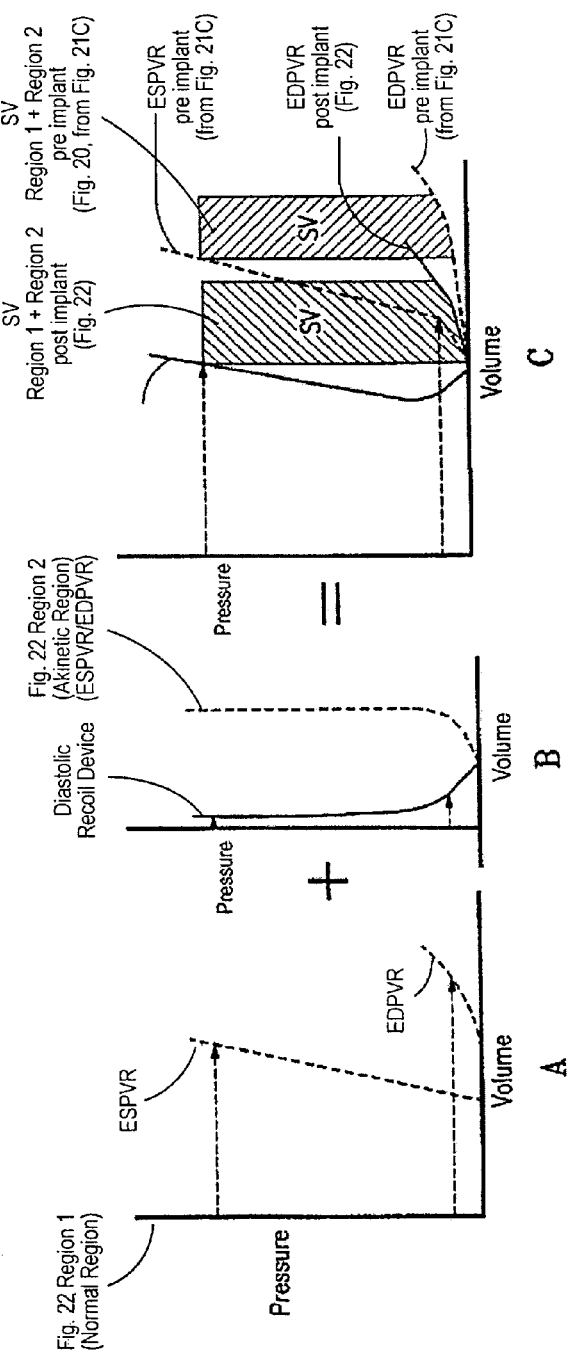
FIGS. 23A-C are diagrammatical representations of the ESPVR and EDPVR of the ventricle of FIG. 22 after treatment according to the present invention, and shows the comparison of the Stroke Volume, pre-implantation and post-implantation.

In the second part of the simulation experiment, the effect is modeled wherein the akinetic Region 2 of a ventricle with diastolic dysfunction (as shown in FIG. 22) of the LV is partitioned by a partitioning device of the invention. The ESPVR and EDPVR for the individual contributions from normal Region 1, the diastolic recoil device, and akinetic Region 2 are represented in FIGS. 23 A and B. The normal Region 1 now exhibits a steeper slope to its ESPVR as the diastolic recoil device isolates Region 2 from Region 1, reducing the overall volume and conferring greater resistance as systole proceeds. The solid line shown in FIG. 23B shows similar information as that in FIG. 19, as it represents the performance of the diastolic recoil device as it is compressed, and the dashed line in FIG. 23B is the ESPVR/EDPVR curve for the akinetic Region 2 in FIG. 22. The new ESPVR and EDPVR for the ventricle as a whole are shown in FIG. 23C, as solid lines. The corresponding ESPVR and EDPVR for the pre-implant ventricle from FIG. 21C are also reproduced in FIG. 23C as dashed lines for comparison. As can be seen in FIG. 23C, the ESPVR and EDPVR curves of the post-implant ventricle (solid lines) are shifted leftwards as compared to the curves of the dilated pre-implant ventricle (FIG. 23C "ESPVR Pre-Implant" and "EDPVR Pre-Implant", dashed lines). However, the ESPVR curve for the partitioned ventricle is shifted more than the EDPVR curve for the partitioned ventricle. This results in increased pump function of the ventricle which can be demonstrated by examining the resultant the pressure-volume loops. The stroke volume (SV) for the ventricle, pre-partitioned (FIG. 20) and partitioned (FIG. 22), are indicated by the shaded volumes labeled "SV Pre-Implant" and "SV Implant". The stroke volume is represented by the width of these shaded volumes as filling proceeds along the EDVPR curves. The right-hand boundary of the stroke volume is the pressure/volume line at end diastole, when isovolumetric contraction begins, and the left-hand boundary is the volume/pressure line representing isovolumetric relaxation during the heart cycle. The partitioned ventricle exhibits increased stroke volume (SV) compared to the dilated, pre-implant ventricle with akinetic Region 2 at comparable end-diastolic and aortic pressures ("SV Implant" vs. "SV Pre-Implant" in FIG. 23C).

Figure 24A:
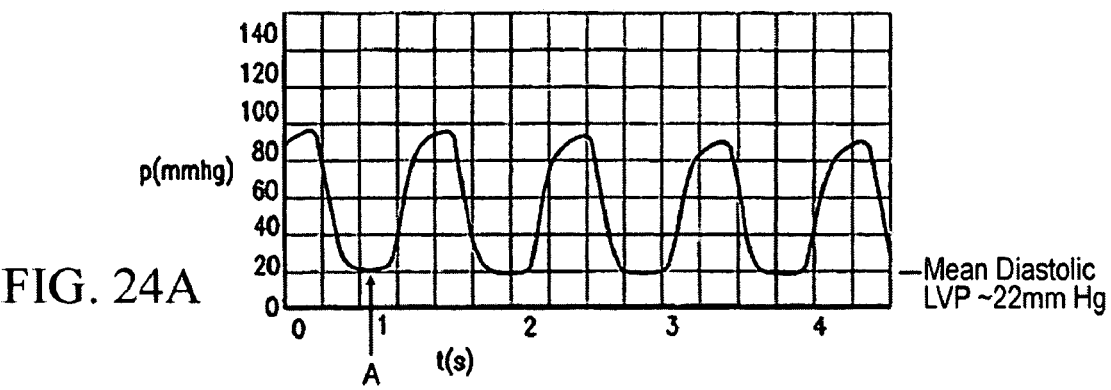
FIG. 24A is a diagrammatical illustration of the left ventricular pressure (LVP) in one dilated ventricle with diastolic dysfunction.
Figure 24B:
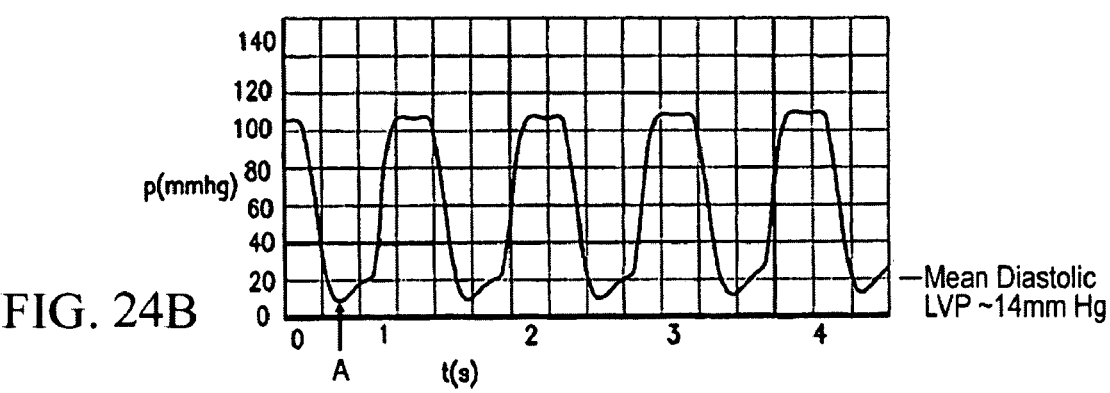
FIG. 24B is one diagrammatical illustration of the left ventricular pressure (LVP) of the ventricle of FIG. 4A after treatment according to the present invention.

FIGS. 24A and 24B, are diagrammatical illustrations of the recordings of the left ventricular pressure (LVP) in one dilated ventricle with diastolic dysfunction before and after implantation of a diastolic recoil device, respectively. In FIG. 24A, diastolic dysfunction results in inefficient filling of the ventricle at relatively high mean diastolic pressure in the ventricle. The akinetic ventricle can neither compress nor expand as effectively as a normal ventricular chamber. The resultant filling pressure at early diastole is therefore higher than in a healthy heart and early filling is decreased. During installation of the diastolic recoil device, the device is anchored to functional portions of the ventricle wall, partitioning the akinetic (nonfunctional) portion of the chamber. This mode of attachment allows the elastic frame of the partitioning device to gain energy from the effectively contracting portion of the ventricular wall, by compressing the elastically resilient frame. As the ventricle relaxes and expands, the energy stored in the frame is released and imparts additional recoil force back to the ventricle wall, which aids in the process of filling the ventricular chamber. As can be seen from FIGS. 24A and 24B, implantation of the diastolic recoil device resulted in decreased minimum diastolic pressures. In this example the minimum LV pressure is decreased by at least 50% (contrasted by points A and A' in FIGS. 24A and 24B respectively) and mean diastolic pressure at least by 10%. The contribution of the elastic energy from the frame assisting expansion of the walls of the ventricle was observed in early diastole, thereby augmenting filling and normalizing diastolic pressure. Decreased mean diastolic pressure of the partitioned ventricle compared to that of the pre-implant ventricle indicates improved diastolic function (mean diastolic LVP of ca. 14 mm Hg in FIG. 24B vs. "mean diastolic LVP of ca. 22 mm Hg in FIG. 24A). These results demonstrate that the diastolic recoil device improves either or both the systolic and diastolic LV function in the remodeled LV with a dysfunctional myocardial region.

The use of a diastolic recoil device and methods of the invention yields a decrease of minimum LV pressure during diastole by at least about 5% up to about 100%. The use of a diastolic recoil device by the methods of the invention yields a decrease of end-diastolic pressure by at least about 5%, and up to about 35%.

Other indicators of LV function may be measured upon installation of the diastolic recoil device. Some of these indicators are hemodynamic measurements, such as, for example, left ventricle end systolic volume index (LVESVI). LVESVI indicates the size of the ventricle at end systole with values normalized to body size. The baseline value for a healthy individual is ~25 ml/m$^2$. LVESVI has significant predictive value for survival outcome, and may represent the most significant correlation used in diagnosis and treatment. In some cases, a patient can be first diagnosed as having heart disease by determining or detecting in that patient a LVESVI greater than 60 ml/m$^2$. Such patient is thus treated by implanting one or more of the devices herein. The diastolic recoil device, by partitioning the ventricle into functional and non-functional portions, causes an initial decrease in LVESVI upon installation. The implantation of the diastolic recoil device may also promote positive remodeling of the ventricle to further decrease ventricle volume as the supported cardiac muscle more effectively contracts and expands, thus decreasing LVESVI by at least 5%.

Left ventricle ejection fraction (LVEF), another hemodynamic measurement, is the percentage of the end diastolic blood volume expelled from the ventricle upon each cardiac cycle. LVEF of 60% or greater are seen in healthy individuals, while an LVEF of 40% is considered the threshold value for diagnosis of heart failure with systolic dysfunction. Implantation of the partitioning device increases the LVEF by at least about 5% and up to about 90%.

Other indices of ventricular function may also be used for diagnosis and for therapeutic follow-up. A number of biochemical markers may be measured and used. One example is NT Pro-Brain Natriuretic Peptide, but many other biological molecules, for example, neurohormones, proteases, and proteins related to distressed or abnormal function may be measured to give quantification of the relative functionality of the ventricle prior and post-implant.

NT-Pro-Brain Natriuretic Peptide (NT-Pro-BNP) is a regulatory peptide that is produced in the ventricle and has been shown to be related to the level of stress in myocardium, as well as involved in adverse remodeling processes seen in late stage disease. A normal NT-BNP level for a healthy individual is generally in the range of 20-30 pg/ml, while in an individual with end stage heart failure, a level can be as high as 2000-3000 pg/ml, and in some instances there may be a correlation between BNP levels and LVEF. The use of NT-Pro-BNP levels as reliable markers for heart disease in a number of patient populations has been proposed (J. L. Januzzi; Cleve. Clin. J. Med., 73(2), 149-52, 155-7, 2006) and may offer advantages in ongoing patient monitoring and care. Thus the present invention contemplates treating a patient by first determining the level of NT-Pro-BNP, and if the level of NT-Pro-BNP is greater than 170 pg/ml (third quartile) or 450 pg/ml (fourth quartile), delivering to such patient one or more of the devices herein. Implantation of a diastolic recoil device improves cardiac function, and decreases the level of NT-Pro-BNP observed post-implant by at least about 10%.

Mitral valve regurgitation can be observed in patients with diastolic dysfunction, and is coupled to poor outcome. Mitral valve regurgitation increases in magnitude as the ventricle increases in size due to pathological dilation. Intervention is often necessary as blood backflow into the atrium leads to accelerated progression of heart failure. Standard therapies include both prescribed medications (i.e. vasodilators like ACE inhibitors and nitrates, and diuretics) and surgical interventions to repair or replace mitral valves. However, these surgical interventions are invasive and may present high risk to the patient. Diastolic recoil device implantation can reverse the decline in ventricular function by decreasing the effective ventricular volume which may obliterate or attenuate the cause of the mitral valve regurgitation. The severity of mitral valve regurgitation is categorized by measuring the regurgitant fraction by, for example, echocardiography. Color Doppler flow on a transthoracic echocardiogram measures the forward flow through the mitral valve during ventricular diastole and compares it to the outflow of blood through the aortic valve in ventricular systole, permitting the calculation of the regurgitant fraction. The present invention contemplates treating a patient by first determining the degree of mitral regurgitation as assessed by the regurgitant fraction and if the regurgitant fraction is at least 20%, delivering to such patient one or more of the devices herein. Diastolic recoil device implantation may therefore benefit patients with mitral valve regurgitation from any clinically relevant cause and decrease the regurgitant fraction by at least about 10%.

Although reference is made to a diastolic recoil device which is implanted in the left ventricle, it is understood by those skilled in the art that such reference is not limiting and similarly suitable diastolic recoil devices may be used in the right ventricle or other heart chambers.

EXAMPLES

Example 1

Symptomatic heart failure patients (New York Heart Association Classification levels II and III) diagnosed with ischemic cardiomyopathy post anterior infarction and systolic dysfunction were enrolled in a study implanting a diastolic recoil device similar to the one shown in FIG. 1. Size selection of the specific device was based on echocardiography comparison with a mean landing zone diameter of 55.1 mm (mean diastolic value or largest value achieved during cardiac cycle). Either 75 mm (3/9 patients) or 85 mm (6/9 patients) diameter devices were installed in a 95.7 minute (mean value) procedure, requiring mean fluoroscope time of 25.5 minutes.

A number of hemodynamic and biochemical variables were examined in each patient before implant and at 90 day post implant and are represented in Table 1 below. Data is available for 4 patients at the 90 day timepoint.

TABLE 1

| Exploratory Endpoints All data as mean values | Baseline (n = 9) Before Implant | 90 days (n = 4) |
|---|---|---|
| LVESVI (ml/m$^2$) | 101.8 | 72.7 |
| LVEF (%) | 29.3 | 37.2 |
| Patients with MR | 5/9 | 1/4 |
| NT-Pro-BNP (pg/ml) | 566 | 393 |

Left ventricle end systolic volume index (LVESVI) in a healthy individual is usually around 25 ml/m$^2$. The mean baseline value for the patient group is notably higher, at 101.8 ml/m$^2$. Significant reduction to 72.7 ml/m$^2$ (~25%) for the LVESVI is observed at 90 days post implant. The ventricle has thus improved in function and was positively remodeled.

Left ventricle ejection fraction (LVEF) in a healthy individual is usually at least 60%. For this group the mean value observed before implantation of the device was 29.3%, slightly less than half of the value seen for healthy patients. At 90 days post intervention an increase in LVEF to 37.2% is observed which is an improvement of about 27%. This is a significant improvement as the threshold value of LVEF to diagnose heart failure is often placed at 40%.

In the overall patient cohort, a significant proportion of the patients (5 of 9) experienced mitral valve regurgitation (MR) prior to implantation. Of four patients who had experienced MR prior to implantation and for whom data at 90 days post implantation is available, three patients had remission of symptoms, with only one patient still experiencing MR. Thus, the improvement in LV function provided by implantation of a diastolic recoil device also provided reduction in MR regurgitation.

NT-Pro-brain Natriuretic peptide (NT-Pro-BNP) levels for a healthy individual are estimated to be in the range of 20-30 pg/ml. In the group of patients analyzed, the baseline mean value of NT-Pro-BNP prior to implantation was 566 pg/ml. This was significantly decreased by the 90 day timepoint to 363 pg/ml, an improvement of about 36%.

In Table 2 below represents data of overall functionality for the individual patients. The 6 minute walk is a simple test which measures the distance a patient is able to traverse during a 6 minutes timed period. The mean distance the patient cohort traveled prior to implant was 328 m. Ninety days post implant, data available for 4 patients shows significant improvement (~44%) to 471 m. The New York Heart Association (NYHA) Classification levels for the patients prior to implantation were Class II/III for this group. At the 90 day timepoint, reassessment of the NYHA Classification was performed on the four patients with available data. Three of the four individuals could be reassigned to less severe disease classifications. Finally, the patients performed a self scoring questionnaire, the Minnesota Living with Heart Failure test (MLHF), and registered significant improvement in self assessment of functionality. Thus, implantation of a diastolic recoil device of this invention demonstrated clear and self evident improvement in function and quality of life for the patient group.

TABLE 2

| Exploratory Endpoints Mean Values | Baseline (n = 9) Before Implant | 90 days (n = 4) |
|---|---|---|
| 6 min walk (m) | 328 | 471 |
| Improvement in NYHA class | — | 3/4 (75%) |
| MLHF | 22.9 | 12.7 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A diastolic recoil device adapted for percutaneous delivery to a heart of a patient comprising a plurality of radially expandable resilient ribs connected at their distal ends to a central hub, and a membrane coupled to said ribs, wherein said ribs are adapted to anchor to a wall of a ventricle of said heart to store energy provided by said ventricle during systole and to provide an elastic recoil force to said wall of said ventricle during diastole.

2. The device of claim 1 further comprising anchor elements on proximal ends of said ribs for anchoring said device to a selected area of said wall of said ventricle.

3. The device of claim 1 further comprising a contact member extending distally from said central hub along a central longitudinal axis of said device, wherein said contact member is adapted to space said central hub of said device a selected distance from a wall of said ventricle.

4. The device of claim 3 wherein said contact member is adapted to contact said wall atraumatically.

5. The device of claim 3 wherein said contact member comprises an atraumatic distal end adapted to distribute pressure against said wall.

6. The device of claim 1 further comprising a hollow connector member extending proximally from said central hub along a central longitudinal axis of said device wherein said connector member is adapted for releasable connection to a delivery catheter.

7. The device of claim 1 further comprising a delayed release spring mechanism adapted to release said elastic recoil force back to said wall of said ventricle at a selected point during diastole.

8. The device of claim 1 wherein an unconstrained diameter of said device is oversized by at least about 10% up to about 60% over a landing zone diameter of said ventricle at end diastole.

9. The device of claim 1 wherein an unconstrained diameter of said device is about 25 mm to about 100 mm.

10. The device of claim 1 further comprising a ring coupled to said ribs near proximal ends of said ribs for sealing said membrane to said wall.

11. A method of treating a patient suffering from a heart condition comprising:
advancing percutaneously a collapsed diastolic recoil device comprising a plurality of radially expandable resilient ribs connected at their distal ends to a central hub, said device further comprising a membrane coupled to said ribs;
expanding said ribs in a ventricle of said heart;
partitioning said ventricle with said membrane; and,
securing said device to opposing walls of said ventricle thereby providing elastic support between said opposing ventricular walls.

12. The method of claim 11 further comprising storing energy provided by said ventricle in said ribs during systole and providing an elastic recoil force to said opposing walls of said ventricle from said ribs during diastole.

13. The method of claim 11 wherein said ribs further comprise anchor elements on proximal ends of said ribs, the method further comprising anchoring said device to a selected area of a wall of said ventricle.

14. The method of claim 11 further comprising spacing said central hub a selected distance from a wall of said ventricle.

15. The method of claim 11 further comprising releasing said device from a delivery catheter.

16. The method of claim 11 further comprising delaying release of an elastic recoil force back to said walls of said ventricle until a selected point after diastole begins.

17. The method of claim 11 wherein an unconstrained diameter of said device is oversized by at least about 10% up to about 60% greater than a landing zone diameter of said ventricle at end diastole.

18. The method of claim 17 wherein said unconstrained diameter of said device is about 25 mm to about 100 mm.

19. The method of claim 11 further comprising restoring overall synchrony in the cardiac cycle.

20. The method of claim 11 further comprising improving ejection fraction of said ventricle by at least about 10%.

21. The method of claim 11 further comprising augmenting movement of said walls of said ventricle during diastole.

22. The method of claim 11 further comprising decreasing stress in said walls of said ventricle, thereby limiting remodeling of said heart.

23. The method of claim 11 further comprising reducing diastolic pressure of said ventricle.

24. The method of claim 11 further comprising improving a pressure-volume relationship of said ventricle.

25. The method of claim 11 further comprising assisting in expansion of said ventricle.

26. The method of claim 11 further comprising supporting a weakened cardiac wall.

27. The method of claim 11 further comprising decreasing left ventricular volume by at least 10%.

28. The method of claim 11 further comprising decreasing minimum left ventricular pressure by at least about 5%.

29. The method of claim 11 further comprising decreasing end-diastolic pressure of said ventricle by at least about 5%.

30. The method of claim 11 further comprising decreasing left ventricle end systolic volume index of said patient by at least about 5%.

31. The method of claim 11 further comprising decreasing the level of NT-Pro-Brain Natriuretic Peptide by at least about 10%.

32. The method of claim 11 further comprising decreasing regurgitant fraction in a patient having mitral valve regurgitation by at least about 10%.

33. The method of claim 11 further comprising sealing said membrane to said walls.

34. A diastolic recoil device comprising a plurality of resiliently deformable ribs and a plurality of anchors, and a membrane coupled to said ribs, said device being adapted to be delivered percutaneously to and anchored within the interior of a ventricle of a patient's heart to span a region of said ventricle, said resiliently deformable member being adapted to deform from a first shape to a second shape during systole and to return to said first shape during diastole to assist in expansion of said ventricle.

35. The device of claim 34 further comprising anchor elements on proximal ends of said ribs for anchoring said device to a selected area of a wall of said ventricle.

36. The device of claim 34 further comprising a contact member extending distally from said central hub along a central longitudinal axis of said device, wherein said contact member is adapted to space said central hub of said device a selected distance from a wall of said ventricle.

37. The device of claim 36 wherein said contact member is adapted to contact said wall atraumatically.

38. The device of claim 36 wherein said contact member comprises an atraumatic distal end adapted to distribute pressure against said wall.

39. The device of claim 34 further comprising a hollow connector member extending proximally from said central hub along a central longitudinal axis of said device wherein said connector member is adapted for releasable connection to a delivery catheter.

40. The device of claim 34 further comprising a delayed release spring mechanism adapted to release an elastic recoil force back to said wall of said ventricle at a selected point during diastole.

41. The device of claim 34 wherein an unconstrained diameter of said device is oversized by at least about 10% up to about 60% over a landing zone diameter of said ventricle at end diastole.

42. The device of claim 34 wherein an unconstrained diameter of said device is about 25 mm to about 100 mm.

43. The device of claim 34 further comprising a ring coupled to said ribs near proximal ends of said ribs for sealing said membrane to a wall of said ventricle.

44. A method of treating a patient suffering from a heart condition comprising:
advancing percutaneously to the interior of a ventricle of the patient's heart a diastolic recoil device comprising a resiliently deformable member and a plurality of anchors;
securing said devices to opposing wall sections of said ventricle with said anchors;
deforming said deformable member as said opposing wall sections move toward each other during systole; and
providing a recoil force from said deformable member to said wall sections during diastole.

45. The method of claim 44 further comprising storing energy provided by said ventricle in said deformable member during systole and providing an elastic recoil force to said wall sections of said ventricle from said deformable member during diastole.

46. The method of claim 44 wherein said device further comprises a membrane coupled to said deformable member, the method further comprising partitioning said ventricle with said membrane.

47. The method of claim 46 further comprising sealing said membrane to said wall sections.

48. The method of claim 44 further comprising releasing said device from a delivery catheter.

49. The method of claim 44 further comprising delaying release of said recoil force back to said walls of said ventricle until a selected point after diastole begins.

50. The method of claim 44 wherein an unconstrained diameter of said device is oversized by at least about 10% up to about 60% greater than a landing zone diameter of said ventricle at end diastole.

51. The method of claim 50 wherein said unconstrained diameter of said device is about 25 mm to about 100 mm.

52. The method of claim 44 further comprising restoring overall synchrony in the cardiac cycle.

53. The method of claim 44 further comprising improving ejection fraction of said ventricle by at least about 10%.

54. The method of claim 44 further comprising augmenting movement of said wall sections of said ventricle during diastole.

55. The method of claim 44 further comprising decreasing stress in said wall sections of said ventricle, thereby limiting remodeling of said heart.

56. The method of claim 44 further comprising reducing diastolic pressure of said ventricle.

57. The method of claim 44 further comprising improving a pressure-volume relationship of said ventricle of said heart.

58. The method of claim 44 further comprising assisting in expansion of said ventricle.

59. The method of claim 44 further comprising supporting a weakened cardiac wall.

60. The method of claim 44 further comprising decreasing left ventricular volume by at least 10%.

61. The method of claim 44 further comprising decreasing minimum left ventricular pressure by at least about 5%.

62. The method of claim 44 further comprising decreasing end-diastolic pressure of said ventricle by at least about 5%.

63. The method of claim 44 further comprising decreasing left ventricle end systolic volume index of said patient by at least about 5%.

64. The method of claim 44 further comprising decreasing the level of NT-Pro-Brain Natriuretic Peptide by at least about 10%.

65. The method of claim 44 further comprising decreasing regurgitant fraction in a patient having mitral valve regurgitation by at least about 10%.

66. A method of treating a patient suffering from a heart condition comprising:
  advancing percutaneously to the interior of a ventricle of the patient's heart a diastolic recoil device comprising a resiliently deformable member and a plurality of anchors;
  securing said device to opposing wall sections of said ventricle with said anchors;
  storing energy within said deformable member as said opposing wall sections move toward each other during systole; and
  releasing energy from said deformable member to said wall sections as said opposing wall sections move away from each other in synchrony with a heart cycle.

67. A method for increasing ejection fraction of the ventricular chamber, comprising:
  inserting an energy storage element into the ventricular chamber storing mechanical energy in the energy storage element during systole of the ventricular chamber and releasing mechanical energy from the energy storage element during diastole of the ventricular chamber.

68. The method of claim 67, wherein storing energy comprises resiliently compressing the energy storage element.

69. The method of claim 67, wherein releases energy comprises resiliently expanding the energy storage element.

70. The method of claim 67, further comprising connecting a resilient cover to a first end of the energy storage element.

71. A device for increasing ejection fraction of a ventricular chamber, comprising:
  an energy storage element configured to be deployed into the ventricular chamber wherein the energy storage element is configured to store mechanical energy by compressing the energy storage element during systole of the ventricular chamber
  and release mechanical energy during diastole of the ventricular chamber.

72. The device of claim 71, wherein the energy storage element is resilient.

73. The device of claim 71, further comprising a cover connected to a first end of the energy storage element.

* * * * *